United States Patent
Vacanti et al.

(10) Patent No.: US 8,357,528 B2
(45) Date of Patent: *Jan. 22, 2013

(54) MICROFABRICATED COMPOSITIONS AND PROCESSES FOR ENGINEERING TISSUES CONTAINING MULTIPLE CELL TYPES

(75) Inventors: Joseph P. Vacanti, Winchester, MA (US); Jeffrey T. Borenstein, Newton, MA (US); Eli Weinberg, Cambridge, MA (US)

(73) Assignees: The General Hospital Corporation, Boston, MA (US); The Charles Stark Draper Laboratory, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/156,675

(22) Filed: Jun. 9, 2011

(65) Prior Publication Data

US 2011/0256619 A1    Oct. 20, 2011

Related U.S. Application Data

(63) Continuation of application No. 10/557,081, filed as application No. PCT/US2004/016059 on May 21, 2004, now Pat. No. 7,960,166.

(60) Provisional application No. 60/472,230, filed on May 21, 2003.

(51) Int. Cl.
    *C12M 1/14*    (2006.01)
(52) U.S. Cl. ............... 435/284.1; 435/297.1; 435/299.1; 435/395
(58) Field of Classification Search .................. None
    See application file for complete search history.

(56) References Cited

U.S. PATENT DOCUMENTS

| | | | |
|---|---|---|---|
| 3,684,097 | A | 8/1972 | Mathewson, Jr. et al. |
| 3,839,204 | A | 10/1974 | Ingenito et al. |
| 3,892,533 | A | 7/1975 | Freedman et al. |
| 3,907,687 | A | 9/1975 | Hoeltzenbein |
| 3,927,981 | A | 12/1975 | Viannay et al. |
| 3,977,976 | A | 8/1976 | Spaan et al. |
| 4,008,047 | A | 2/1977 | Petersen |
| 4,176,069 | A | 11/1979 | Metz et al. |
| 4,191,182 | A | 3/1980 | Popovich et al. |
| 4,229,290 | A | 10/1980 | Raj |
| 4,636,310 | A | 1/1987 | Bellhouse |
| 4,666,668 | A | 5/1987 | Lidorenko et al. |
| 5,034,188 | A | 7/1991 | Nakanishi et al. |
| 5,061,620 | A | 10/1991 | Tsukamoto et al. |
| 5,110,548 | A | 5/1992 | Montevecchi |

(Continued)

FOREIGN PATENT DOCUMENTS

| DE | 10000823 A1 | 7/2001 |
|---|---|---|
| EP | 0246675 A1 | 11/1987 |

(Continued)

OTHER PUBLICATIONS

Supplementary European Search Report dated Feb. 19, 2007, for EP 04809403.

(Continued)

*Primary Examiner* — Allison Ford
(74) *Attorney, Agent, or Firm* — Edwards Wildman Palmer LLP; Peter C. Lauro, Esq.; George N. Chaclas, Esq.

(57) ABSTRACT

The present invention relates to a three-dimensional system, and compositions obtained therefrom, wherein individual layers of the system comprise channels divided longitudinally into two compartments by a centrally positioned membrane, and wherein each compartment can comprise a different cell type.

8 Claims, 21 Drawing Sheets

U.S. PATENT DOCUMENTS

| | | | |
|---|---|---|---|
| 5,204,055 A | 4/1993 | Sachs et al. |
| 5,222,982 A | 6/1993 | Ommaya |
| 5,225,161 A | 7/1993 | Mathewson et al. |
| 5,263,924 A | 11/1993 | Mathewson |
| 5,266,480 A | 11/1993 | Naughton et al. |
| 5,308,356 A | 5/1994 | Blackshear, Jr. et al. |
| 5,316,724 A | 5/1994 | Mathewson et al. |
| 5,443,950 A | 8/1995 | Naughton et al. |
| 5,486,359 A | 1/1996 | Caplan et al. |
| 5,518,680 A | 5/1996 | Cima et al. |
| 5,601,727 A | 2/1997 | Bormann et al. |
| 5,626,759 A | 5/1997 | Krantz et al. |
| 5,665,596 A | 9/1997 | Mussi |
| 5,686,289 A | 11/1997 | Humes et al. |
| 5,695,717 A | 12/1997 | Polaschegg et al. |
| 5,785,964 A | 7/1998 | Naughton et al. |
| 5,843,780 A | 12/1998 | Thomson |
| 5,849,553 A | 12/1998 | Anderson et al. |
| 5,885,829 A | 3/1999 | Mooney et al. |
| 5,888,248 A | 3/1999 | Berg et al. |
| 5,906,828 A | 5/1999 | Cima et al. |
| 6,022,743 A | 2/2000 | Naughton et al. |
| 6,045,818 A | 4/2000 | Cima et al. |
| 6,107,043 A | 8/2000 | Jauregui et al. |
| 6,136,212 A | 10/2000 | Mastrangelo et al. |
| 6,139,574 A | 10/2000 | Vacanti et al. |
| 6,143,293 A | 11/2000 | Weiss et al. |
| 6,165,486 A | 12/2000 | Marra et al. |
| 6,183,781 B1 | 2/2001 | Burke |
| 6,197,575 B1 | 3/2001 | Griffith et al. |
| 6,200,802 B1 | 3/2001 | Greene et al. |
| 6,228,607 B1 | 5/2001 | Kersten et al. |
| 6,246,466 B1 | 6/2001 | Hirano et al. |
| 6,287,558 B1 | 9/2001 | Lanza et al. |
| 6,372,482 B1 | 4/2002 | Mitrani |
| 6,376,169 B1 | 4/2002 | Adams et al. |
| 6,455,311 B1 | 9/2002 | Vacanti |
| 6,458,275 B1 | 10/2002 | Shukla et al. |
| 6,479,064 B1 | 11/2002 | Atala |
| 6,479,072 B1 | 11/2002 | Morgan et al. |
| 6,525,242 B1 | 2/2003 | Wu et al. |
| 6,542,858 B1 | 4/2003 | Grass et al. |
| 6,547,994 B1 | 4/2003 | Monkhouse et al. |
| 6,573,063 B2 | 6/2003 | Hochman |
| 6,607,910 B1 | 8/2003 | Dimitrijevich et al. |
| 6,645,715 B1 | 11/2003 | Griffith et al. |
| 6,647,358 B2 | 11/2003 | Grass et al. |
| 6,942,873 B2 | 9/2005 | Russell et al. |
| 7,048,856 B2 | 5/2006 | Fissell, IV et al. |
| 7,191,110 B1 | 3/2007 | Charbel et al. |
| 7,371,400 B2 | 5/2008 | Borenstein et al. |
| 7,759,113 B2 | 7/2010 | Vacanti et al. |
| 7,776,021 B2 | 8/2010 | Borenstein et al. |
| 7,955,504 B1 | 6/2011 | Jovanovic et al. |
| 8,128,822 B2 | 3/2012 | Browning et al. |
| 8,137,554 B2 | 3/2012 | Jovanovic et al. |
| 2001/0041964 A1 | 11/2001 | Grass et al. |
| 2002/0010550 A1 | 1/2002 | Grass et al. |
| 2002/0013662 A1 | 1/2002 | Grass et al. |
| 2002/0035459 A1 | 3/2002 | Grass et al. |
| 2002/0055092 A1 | 5/2002 | Hochman |
| 2002/0061540 A1 | 5/2002 | Grass et al. |
| 2002/0090725 A1 | 7/2002 | Simpson et al. |
| 2002/0106311 A1 | 8/2002 | Golbig et al. |
| 2002/0160471 A1 | 10/2002 | Kisiday et al. |
| 2002/0182241 A1 | 12/2002 | Borenstein et al. |
| 2003/0075498 A1 | 4/2003 | Watkins et al. |
| 2003/0113708 A1 | 6/2003 | Flint et al. |
| 2003/0121594 A1 | 7/2003 | Brill |
| 2003/0124099 A1 | 7/2003 | Atala |
| 2003/0125252 A1 | 7/2003 | Underhill et al. |
| 2003/0129736 A1 | 7/2003 | Mitrani |
| 2003/0173965 A1 | 9/2003 | Oesingmann |
| 2003/0215941 A1 | 11/2003 | Campbell et al. |
| 2004/0057869 A1 | 3/2004 | Dingley |
| 2004/0084370 A1 | 5/2004 | Singh et al. |
| 2004/0147016 A1 | 7/2004 | Rowley et al. |
| 2005/0169962 A1 | 8/2005 | Bhatia et al. |
| 2005/0202557 A1 | 9/2005 | Borenstein et al. |
| 2006/0018838 A1 | 1/2006 | George et al. |
| 2006/0136182 A1 | 6/2006 | Vacanti et al. |
| 2007/0125489 A1 | 6/2007 | Paul et al. |
| 2007/0128171 A1 | 6/2007 | Tranquillo et al. |
| 2007/0281353 A1 | 12/2007 | Vacanti et al. |
| 2010/0022936 A1 | 1/2010 | Gura et al. |
| 2010/0098742 A1 | 4/2010 | Vacanti et al. |
| 2010/0267136 A1 | 10/2010 | Vacanti et al. |
| 2010/0326914 A1 | 12/2010 | Drost et al. |
| 2010/0326916 A1 | 12/2010 | Wrazel et al. |
| 2011/0056882 A1 | 3/2011 | Borenstein et al. |
| 2012/0074062 A1 | 3/2012 | Jovanovic et al. |

FOREIGN PATENT DOCUMENTS

| | | |
|---|---|---|
| EP | 03718019 | 3/2003 |
| JP | 60-181654 A | 9/1985 |
| JP | 6237992 A | 8/1994 |
| WO | WO-9609423 | 3/1996 |
| WO | WO-9640002 | 12/1996 |
| WO | WO-9952356 | 10/1999 |
| WO | WO-0011407 | 3/2000 |
| WO | WO-0038758 A1 | 7/2000 |
| WO | WO-00/66036 | 11/2000 |
| WO | WO-0111011 | 2/2001 |
| WO | WO-02076529 A1 | 10/2002 |
| WO | WO-03029880 | 4/2003 |
| WO | WO-03061585 | 7/2003 |
| WO | WO-200401098 | 12/2003 |
| WO | WO-2004020341 A2 | 3/2004 |
| WO | WO-2010009307 A2 | 1/2010 |

OTHER PUBLICATIONS

Borenstein, et al: "Microfabrication technology for vascularized tissue engineering", Biomedical Microdevices Kluwer Academic Publishers, USA, vol. 4, No. 3, Jul. 2002, pp. 167-175.

Kaihara, et al: "Silicon micromachining to tissue engineer branched vascular channels for liver fabrication", Tissue Engineering, Apr. 2002, vol. 6, No. 2, Apr. 2000, pp. 105-117.

Borenstein, et al: "Microfabricated biodegradable scaffolds for tissue engineering of vital organs", Architecture and Application of Biomateials and Biomolecular Materials. Symposium (Mater. Res. Soc. Symposium Proceedings vol. EXS-1) Mater. Res. Soc. Warrendale, PA, USA 2004, pp. 9-11.

J. Borenstein "Proceedings of the 12th International Conference on Solid State Sensor" *Transducer* pp. 1754-1577 (2003).

Supplementary European Search Report, for EP 03718019, dated Jun. 11, 2007.

M. J. Hass et al. "Breathing Life into Lung Models" SciBX3(28); doi: 10.1038/scibx.2010.847; published online Jul. 22, 2010 (<http://www.nature.com/scibx/journal/v3/n28/full/scibx.2010.847.html>).

Jaeger, Introduction to Microelectronic Fabrication, Addison-Wesley Pub. Co., Reading, MA 1988, vol. V, Chapter I, pp. 1-12.

Den Braber, et al., "Orientation of ECM protein deposition, fibroblast cytoskeleton, and attachment complex components on silicone microgrooved surfaces", Journal of Biomedical Materials Research, vol. 40, No. 2, May 1998, pp. 291-300.

O. Schueller, et al., "Fabrication and Characterization of Glassy Carbon MEMS", Chem. Mater., 1997, vol. 9, pp. 1399-1406.

N. Patel, et al., "Spatially controlled cell engineering on biodegradable polymer surfaces", The FASB Journal, vol. 12, Nov. 1998, pp. 1448-1454.

S. Huang, et al., "Control of Cyclin D1, p27Kip1 and Cell Cycle Progression in Human Capillary Endothelial Cells by Cell Shape and Cytoskeletal Tension", Molecular Biology of the Cell, Nov. 1998, vol. 9, pp. 3179-3193.

E. Delamarche, et al., "Patterned Delivery of Immunoglubulins to Surfaces Using Microfluidic Networks", Science, vol. 276, May 2, 1997, pp. 779-781.

C. Chen, et al., "Geometric Control of Cell Life and Death", Science, May 30, 1997, vol. 276, pp. 1425-1428.

Y. Xia, et al., "Micromolding of Polymers in Capillaries: Applications in Microfabrication", Chem. Mater. 1996, vol. 8, pp. 1558-1567.

E. Delamarche, et al., "Microfluidic Networks for Chemical Patterning of Substrates: Design and Application to Bioassays", J. Am. Chem. Soc. 1998, vol. 120, pp. 500-508.
A. Folch et al., "Molding of Deep Polydimethylsiloxane Microstructures for Microfluidics and Biological Applications", Journal of Biomechanical Engineering, Feb. 1999, vol. 121, pp. 28-34.
K. Heselmeyer, et al., "Gain of Chromosome 3q defines the transition from severe dysplasia to invasive carcinoma of the uterine cervix", Proc. Natl. Acad. Sci. USA, vol. 93, Jan. 1996, pp. 479-484.
E. Kim, et al., "Polymer microstructures formed by moulding in capillaries", Nature, vol. 376, Aug. 17, 1995, pp. 581-584.
O. Schueller, et al., "Fabrication of Glassy Carbon Microstructures by Pyrolisis of Microfabricated Polymeric Precursors", Adv. Mater., 1997, vol. 9, No. 6, pp. 477-480.
M. Trau, et al., :"Microscopic patterning of orientated mesoscopic silica through guided growth", Nature, vol. 390, Dec. 1997, pp. 674-676.
M. Bailly et al., "Regulation of Protrusion Shape and Adhesion to the Substratum during Chemotactic Responses of Mammalian Carcinoma Cells", Experimental Cell Research, vol. 241, (1998), pp. 285-299 (Article No. EX984031).
Thompson, et al; "A Novel Pulsatile, Laminar Flow Bioreactor for the Development of Tissue-Engineered Vascular Structures"; Tissue Engineering, vol. 8, No. 6, 2002, pp. 1083-1088.
Liu, et al; Characterization and Evaluation of Detoxification Functions or a Nontumorigenic Immortalized Porcine Hepatocyte Cell Line (HepLiu$^1$); Cell Transplantation, vol. 8, 1999, pp. 219-232.
Griffith, et al; "In Vitro Organogenesis of Liver Tissue"; Bioartificial Organs, vol. 831 of the Annals of the New York Academy of Sciences, Dec. 31, 1997, pp. 382-397.
Ames, et al; "Methods for Detecting Carcinogens and Mutagens with the *Salmonella/Mammalian-Micorsome* Mutagenicity Test"; Mutation Research, 31 (1975), pp. 347-364.
Griffith, et al., Annals of Biomed. Eng., 26 (1998).
King, Kevin R.., et al., "Biodegradable Microfluidics", Advanced Materials, 2004, 16, No. 22, Nov. 18.
Shin, Michael et al., "Hybrid Bio/Artifical Microdevices", Biomedical Microdevices 6:4, 269-278, 2004.
Fidkowski, Christina et al., "Endothelialized Microvasculature Based on a Biodegradable Elastomer", Tissue Engineering, vol. 11, No. ½, 2005.
Wang, Gou-Jen, et al., "Structure optimization of microvascular scaffolds", Biomed Microdevices (2005) 10: 51-58.
Kassab, Ghassan S. et al., "Morphometry of pig coronary arterial trees", American Physiological Society, 1993, 0363-6135/93.
Carraro, Amedeo et al., "In vitro analysis of a hepatic device with intrinsic microvascular-based channels", Biomed Microdevices (2008) 10:795-805.
Allen et al., Tissue Engineering (2002), vol. 8, No. 5, pp. 725-737.
Godbey et al., Ann NY Acad Sci (2002), vol. 961, pp. 10-26.
"Tissue" Merriam-Webster Online Dictionary, (2009), Merriam-Webster Online, May 21, 2009 URL; <http://www.m-w.com/dictionary/tissue>.
Marler J., et al., "Transplantation of cells in matrices for tissue regeneration", Advanced Drug Delivery Reviews, vol. 33. pp. 165-182, 1998.
Bell et al., Science 221, 1052 (1981).
Burke et al., Ann Surg 194, 413 (1981).
Langer, et al., Science 260, 920(1993).
Vacanti et al., Materials Research Society 252, 367 (1992).
Vacanti, et al., Lancet 354, 32 (1999).
Xu et al., Nat. Biotechnol., 19, 971 (2001).
Keller, et al., (1999) Exp. Hematol. 27:777-787.
Marti, et al., (1995) Nature. 375:322-325.
Prelle, et al., (2000) Biochem. Biophy. Res. Commun. 277:631-638.
Hardt, et al., (1985) Eur. J. Immunol. 15:472-478.
Huelsken, et al., (2001) Cell. 105:533-545.
Ji, et al., (2000) J. Bone Miner. Metab. 18:132-139.
Migliorati, et al., (1987) J. Immunol. 138:3618-3625.
Eghbali, et al., (1991) Proc. Natl. Acad. Sci. USA. 88:795-799.
Niijima, et al., (1995) J. Neurosci. 15:1180-1194.
Guo, et al., (1997) Dev. Biol. 184:61-69.
Ling, et al., (1998) Exp. Neurol. 149:411-423.
Lopez-Fernandez, et al., (2000) J. Biol. Chem. 275:21653-60.
Wang, et al., (1998) Leuk. Res. 13:1091-1097.
Lako, et al., (2001) Mech. Dev. 103:49-59.
Evans, et al., (1981) Nature 292: 154-156.
Matsui, et al., (1991) Nature 353:750-2.
Thomson, et al., (1995) Proc. Natl. Acad. Sci. USA 92:7844-8.
Thomson , et al., (1998) Science 282:1145-1147.
Shamblott, et al., (1998) Proc. Natl. Acad. Sci. USA 95:13726-31.
Mitaka, et al., Biochem Biophy Res Commun 214, 310 (1995).
Taneto, et al., Am Jpathol 148, 383 (1996).
Mitaka, et al., Hepatology 29, 111 (1999).
Teebken, et al., Eur J. Vasa Endovasc. Surg. 19, 381 (2000).
Ranucci, et al., Biomaterials 21, 783 (2000).
Burg, et al., J. Biomed. Mater. Res. 51, 642 (2000).
Rennie, J. Scientific American 280, 37 (1999).
Lysaght, et al., Tissue Eng 4(3), 231 (1998).
Amedee, et al., Differentiation, 58:157-164 (1994).
Burke, et al., Ann Surg 194, 413 (1981).
Compton, et al., Laboratory Investigation 60, 600 (1989).
Parenteau, et al., Journal of Cellular Biochemistry 45, 24 (1991).
Parenteau, et al., Biotechnology and Bioengineering 52, 3 (1996).
Purdue, et al., J. Burn Care Rehab 18, 52 (1997).
Hansbrough, et al., Clinical Plastic Surg 25, 402 (1998).
Vacanti, et al., Materials Research Society 252, 367 (1992).
Kane, et al., Biomaterials, 20, 2363 (1999).
Griffith, et al., Annals of Biomed. Eng. 831 (1997).
Folch, et al., Biotechnology Progress, 14, 388 (1998).
Eiselt, et al., Biotechnology. Prog. 14, 134 (1998).
Wang, et al., Nature Biotech 20, 602 (2002).
Runyan, et al., Semiconductor Integrated Circuit Processing Technology (Addison-Wesley Publishing Co., Reading, MA 01990); Proceedings of the IEEE Micro Electro Mechanical Systems Conference, 1987-1998.
Jansen, et al., The Black Silicon Method IV: The Fabrication of the Three-Dimensional Structures in Silicon with High Aspect Ratios for Scanning Probe Microscopy and Other Applications, IEEE Proceedings of Micro Electro Mechanical Systems Conference, pp. 88-93 (1995).
Frazier, et al., "Two dimensional metallic microelectrode arrays for extracellular stimulation and recording of neurons":, IEEE Proceedings of the Micro Electro Mechanical Systems Conference, pp. 195-200 (1993).
Lehmann, Porous Silicon—A New Material for MEMS:, IEEE Proceedings of the Micro Electro Mechnaical Systems Conference, pp. 1-6 (1996).
Laermer, et al., "Bosch Deep Silicon Etching: Improving Uniformity and Etch Rate for Advanced MEMS Applications", Micro Electio Mechnaical Systems, Orlando, FL, USA (Jan. 17-21, 1999).
Despont, et al., "High-Aspect-Ratio, Ultrathick, Negative-Tone Near-UV Photoresist for MEMS", Proc. Of IEEE 10th Annual International Workshop on MEMS, Nagoya, Japan, pp. 518-522 (Jan. 26-30, 1997).
Henry, et al., "Micromachined Needles for the Transdermal Delivery of Drugs", Micro Electro Mechnaical Systems, Heidelberg, Germany, pp. 494-498 (Jan. 26-29, 1998).
A.A. Ayon, et al., "Tailoring Etch Directionality in a Deep Reactive Ion Etching Tool", J. Vac. Sci. Tech., B 18, 1412 (2000).
Sachs, et al., Manufacturing Review 5, 117-126 (1992).
Jo et al., SPIE 3877, 222 (1999).
Camporese, et al., IEEE Electron, Device Lett. EDL 2, 61 (1981).
Block, et al., J Cell Biol, 132, 1133 (1996).
Landry, et al., J Cell Biol, 101, 914 (1985).
Nishikawa, et al., Exp Cell Res. 223, 357 (1996).
Uyama, et al., Transplantation 55, 932 (1993).
Braber, Den, et al., J. Biomed. Matter. Res. 40, 291 (1998).
Aiken, et al., J. Pediatr Surg 25, 140 (1990).
Seglen, Methods Cell Biol 13, 29 (1976).
Schwerer, et al., Clinica Chemica Acta 163, 237 (1987).
Peterson, Je J Patol Bacteriol 89, 153 (1965).
Duffy, et al., Anal. Chem. 70, 4974 (1998).
Mitaka, et al., Gasroenterol Hepatol 13 Suppl., S70 (1998).
Tateno, et al., Am J Pathol 149, 1593 (1996).

Laconi, et al., Am J. Pathol 153, 319 (1998).

Hansborough et al., (1998) "Skin Replacements", Clin. Plast. Surg. 25(3): 407-23.

Henry, et al. (1998) "Micromachined Needles for the Transdermal Delivery of Drugs", The Eleventh Annual International Workshop.

Kourepenis et al., (1998), "Performance of MEMS Inertial Sensors", Position Location and Navigation Symposium, Aerospace & Electronic Systems Society, Palm Springs, California, Apr. 20-23, 1996.

McWhorter, et al. (1997) "vol. 2: Micromachining and Trends for the Twenty-First Century" Handbook of Microlithography, Micromachinery and Microfabriation. Ed. P. Rai-Choudhury, Bellingham, WA: SPIE Press.

Renie, J. ed. (1999) Special Report: The promise of Tissue Engineering. Scientific American 280: 37.

Vacanti, et al. (1992) "Tissue-Inducing Biomaterials", Material Research Society Symposium Proceedings 252: 367.

Langer et al., (1993) "Tissue Engineering", Science 260 (5110): 920-6.

Langer et al., (1999) "Tissue Engineering: The Obstacles to Building New Organs for, Cells and Synthetic Polymers are Daunting but Surmountable", Scientific American 280, 86-89.

Sunback et al., "Alternatives to Liver Transplantation: From Hepatocyte Transplantation to Tissue Engineering Organs", Gastroenterology 118: 438-442(2000).

Lim, et al., Lab Chip (2003), 3: 318-323.

Iwasaki et al., Science Direct (Aug. 2002), 23/16: 3421-3427.

Biomedical Materials; Polyimide membrane for use as artificial lung material, www.highbeam.com/doc/1G1-45103565.html, (Nov. 1, 1994).

CROSS, "Fractals in Pathology". Journal of Pathology 182: 1-8 (1997).

Anderson et al., "Fabrication of Topologically Complex Three-Dimensional Microfluidic Systems in PDMS by Rapid Prototyping". Anal. Chem 72: 3158-3164 (2000).

Hediger et al. "Biosystem for the Culture and Characterization of Epithelial Cell Tissues". Sensors and Actuators B 63: 63-73 (2000).

Borenstein et al. "Living Three-Dimensional Microfabricated Constructs for the Replacement of Vital Organ Funcgtion". Transducers 4C1.3: 1754-1757 (2003).

Stone "Microfluidics: Basic Issues, Applications, and Challenges". American Institute of Chemical Engineers Journal 47(6): 1250-1254 (2001).

Fairley "Blood from a Chip". Technology Review; p. 28 (2000).

Aggregated porous solid

MICROFABRICATED COMPOSITIONS AND PROCESSES FOR ENGINEERING TISSUES CONTAINING MULTIPLE CELL TYPES

CROSS-REFERENCE TO RELATED APPLICATIONS

This application is a continuation of application Ser. No. 10/557,081 now U.S. Pat. No. 7,960,166, which is the U.S. national phase, pursuant to 35 U.S.C. §371, of PCT international application Ser. No. PCT/US2004/016059, filed May 21, 2004, designating the United States and published in English on Apr. 21, 2005 as publication WO/2005/034624, which claims priority from U.S. Provisional Patent Application Ser. No. 60/472,230, filed on May 21, 2003. The entire contents of the aforementioned patent applications are incorporated herein by this reference.

Reference is also made herein to International Application No. PCT/US2004/001098, filed Jan. 16, 2004, that published in English on Aug. 5, 2004 as publication WO/2004/065616. Reference is also made herein to U.S. Ser. No. 10/187,247, filed Jun. 28, 2002, now U.S. Pat. No. 7,759,113, which claims priority to U.S. Ser. No. 60/367,675, filed Mar. 25, 2002, and which is a CIP of Ser. No. 09/560,480, filed Apr. 28, 2000, now U.S. Pat. No. 6,455,311, which claims priority to U.S. Ser. No. 60/165,329, filed Nov. 12, 1999 and to U.S. Ser. No. 60/131,930, filed Apr. 30, 1999, the contents each of which are expressly incorporated herein by reference. Reference is also made herein to U.S. Ser. No. 10/528,737, which is the U.S. national phase of International Appln. No. PCT/US2003/029880, filed Sep. 23, 2003, that published in English on Apr. 1, 2004 as publication WO/2004/026115, which claims priority to U.S. Ser. No. 60/412,981, filed on Sep. 23, 2002, and U.S. Ser. No. 60/449,291, filed on Feb. 21, 2003, the contents of each of which are expressly incorporated herein by reference.

STATEMENT OF GOVERNMENT INTEREST

The United States government has certain rights in this invention by virtue of grant number DAMD-17-02-2-0006.

Each of the applications and patents cited in this text, as well as documents or references cited in each of the applications and patents (including during the prosecution of each issued patent; "application cited document") and each of the PCT and foreign applications and patents, and each of the documents cited or referenced in each of the application cited documents, are hereby expressly incorporated herein by reference, and may be employed in the practice of the invention. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference. Documents incorporated by reference into this text or any teaching therein can be used in the practice of this invention. Documents incorporated by reference into this text are not admitted to be prior art. Furthermore, author or inventors on documents incorporated by reference into this text are not to be considered to be "another" or "others" as to the present inventive entity and vice versa, especially where one or more authors or inventors on documents incorporated by reference into this text are an inventor or inventors named in the present inventive entity.

FIELD OF THE INVENTION

The present invention relates to a three-dimensional tissue engineered system, and compositions obtained therefrom, wherein individual layers of the system comprise channels having multiple cell types (e.g., organ-specific cells and a vascular supply) divided by membrane.

BACKGROUND OF THE INVENTION

Methods of achieving organ substitution involve three broad classes of approaches. In the first, replacement organs are realized by the construction of electromechanical devices, such as the recently developed, wholly implantable mechanical replacement heart. A second alternative involves the use of xenotransplantation, or animal organs, rather than human donor organs. The third general category of providing replacement function for tissues and organs involves the rapidly emerging field of tissue engineering.

The principal disadvantages of mechanical devices and xenotransplantation involve the challenges of integrating these devices and tissues within the host. In the former case, mechanical devices utilize materials that are foreign to the host and therefore engender processes such as inflammation and clotting. Additionally, mechanical devices are inherently temporary in nature, since they require artificial power supplies, control circuitry and other features that can never fully integrate into a natural system. In the case of xenotransplantation, the human immune system is designed to reject cells and tissues from foreign species and therefore, immune system suppression and its inherent risks remain a challenge. Additional risks involve the transmission of genetic viruses from the donor animal to the host.

Tissue engineers have taken several approaches to generate replacement tissues and organs in the laboratory. Generally, autologous tissue (from cells taken from the organ recipient) are seeded onto a scaffold and expanded in culture. This scaffold must be biologically compatible to avoid inflammatory responses and rejection of the implanted device, and may be biodegradable so that the artificial material bioresorbs, leaving only natural tissue. Scaffold fabrication techniques include an array of polymer processing techniques such as molding, casting, fiber mesh fabrication, and solid freeform fabrication. All of these methods lack the resolution necessary to fashion the finest features of the organ, such as the capillaries, which predominate the circulatory supply. More recent developments in microfabrication technology, such as MEMS (MicroElectroMechariical Systems), which includes silicon micromachining and polymer replica molding, have improved construction of artificial tissue and organ scaffolds. Typically, the resolution of these techniques is in the 10 nun-1-micron range, well in the range of what is necessary to configure the highest fidelity features of an organ.

Within the field of tissue engineering, two basic methods for organizing cells into tissue structures and organs are being pursued. For most tissues and organs, multiple cell types are required; the most significant requirement in addition to the need for replacement of specific organ function is the cellular component of the vascular supply, which nourishes the tissue. One such class of methods utilizes biochemical factors, chemical gradients, growth factors and other chemical means to arrange multiple cell types on a substrate. These chemical techniques may involve the micropatterning of the scaffold surface for cell and tissue engineering with surface chemistries, which enhance adhesion, growth, alignment and other behaviors of specific cell types.

The second broad class of methods utilizes precision loading of specific cell types into separate microengineered compartments within the tissue-engineered structure. Such an approach often invokes microfluidic loading, either dynamically or statically, of a network of channels or vessels connected to form a cell compartment, with a semi-permeable barrier that physically separates cells from all other compartments. In sequential fashion, each compartment of a bilayer structure is loaded with the specific cell type, and communication between compartments is controlled by porous or nonporous barriers (J. T. Borenstein, et al. Proc. 12th Int'l. Conf. Solid State Sensors, Actuators and Microsystems (Transducers 2003), 1754-7 (2003)). Properties of the barrier material are governed by the requirements of the specific cells and tissues in adjacent compartments. For instance, in the case of organ-specific cells such as hepatocytes contained in a compartment adjacent to the endothelial cells comprising the vascular supply, the barrier material, or membrane, must physically separate the cell types from adjacent compartments during cell seeding, but must readily enable the transfer of oxygen, nutrients and waste products between the two compartments.

This microfabrication process is inherently two-dimensional in nature, and one way to construct a three-dimensional tissue engineered device is to stack multiple layers of cell sheets, with microfabricated membranes interspersed between these layers. The interspersed membranes contain pores that govern the transport properties of the film; the pore size, porosity and permeability of the membrane are controlled to provide the appropriate behavior for the desired application. The stacking process proceeds as follows: a microfabricated polymer film imprinted with a pattern for the compartment containing organ-specific cells, such as hepatocytes, is placed at the bottom of the stack. Next, a membrane with controlled transport properties is placed over the compartment, and bonded to the compartment layer. Next, a microfabricated polymer film with vascular channels imprinted (face down) is placed over the membrane, and bonded to it. In this manner, cells loaded into the lower compartment communicate with the vascular channels located above it by transport through the membrane. Three-dimensional integration of this assembly is achieved by situating vertical through-holes within each of the layers, thus forming "pipes" along the z-axis. Pipes for the organ-specific compartment are connected laterally to the compartments within each organ-specific layer, but are separated from the pipes associated with integration of the vascular layers.

One of the principal drawbacks of the foregoing approach involves the restrictions on the design of organ structures. For instance, the stacking approach described above results in capillary beds that are oriented laterally within the polymer film containing the vascular network but does not allow for vertically oriented blood vessels other than the inflow and outflow pipes integrating the entire network. This restriction results in a limited density of capillaries within the three-dimensional structure; the ratio of small blood vessels to large vessels is not nearly as high as it is in physiological systems.

Thus, there remains a need in the art for devices and methods that can replicate the requisite features of the organ it is replacing, such as the fluid dynamics of the vascular supply and other organ structures.

SUMMARY OF THE INVENTION

To address obstacles in the art, compositions and methods of the invention provide a three-dimensional system comprising repeating layers, wherein an aggregate of cell types can be contained in a single layer.

The present invention differs from former approaches, which require three separate layers, one for the vascular network, one for the membrane, and one for the organ-specific (e.g., parenchymal cells), in order to build a single "unit cell" for stacking. The present invention incorporates each of these three layer functions into a single layer, integrated with adjacent layers, greatly reducing the complexity of the device fabrication. Former methods also require that vascular and parenchymal cells be arranged on separate polymer films, separated by a semipermeable membrane in the z-axis. Systems of the present invention divide the vascular and parenchymal cells with micropores or nanopores connecting the cell compartments within the same layer. As a result, the total volume of polymer is reduced by as much as a factor of three, since roughly the same number of total cells are contained within one polymer film rather than the three layers making up each organ subunit.

Accordingly, in one embodiment, the present invention provides a three-dimensional system comprising at least two layers, wherein each layer comprises channels divided longitudinally into two compartments by a centrally positioned membrane. Each compartment can comprise a different cell type (e.g., organ-specific cells in one compartment and a vascular supply in the second compartment). As a result, an aggregate of cell types can be contained in a single layer, which is then integrated into a multi-layer system.

In a further embodiment, cell types on each side of the membrane can align vertically with the same cell type contained in the adjacent layer.

Each layer of the system will have a support element, comprising a surface in which the channels are formed. The support element can comprise a mold, and/or a polymer scaffold. The support element can be made of nondegradable polymers such as PolyDiMethylSiloxane (PDMS), PolyMethylMethacrylate (PMMA), or can comprise biodegradable materials such as PolyCaproLactone (PCL), or biorubber, but the invention is not so limited.

In yet another embodiment, a sealant can be placed over the channels. The sealant can be made of the same or different material used to form the support element. The membrane can be semi-permeable and can function as a filter. The membrane can be made of a biologically compatible, nondegradable material such as PolyDiMethylSiloxane (PDMS), PolyMethylMethacrylate (PMMA), PolyEtherSulfone (PES), PolyCarbonate (PC), or from a degradable material such as polylactide-co-glycolide (PLGA), PolyCaproLactone (PCL) or Biorubber, but the invention is not so limited. Each layer can further comprise connections for inflow and outflow. In another embodiment, the membrane comprises nano-scale pores through which flow between the compartments is conducted. Pores can range from a few nanometers to a few microns in diameter, depending upon the filtration requirements and the fabrication process used to produce the membranes. Preferably, the pores are between 100 nanometers and 2 microns. Pores can also be less than 100 nanometers.

In yet another embodiment, the membrane can be fortified by a solid material added to the system. The solid material can incorporate into the membrane, providing additional support, or altering the geometry or transport properties of the pores in a controlled way. The solid material can be a porous solid, including but not limited to, collagen (e.g., Matrigel™), fibronectin, laminin, or self-assembling peptides, but the invention is not so limited. In one embodiment, the solid material can incorporate into the nano-pore, to further subdivide the area in which flow between compartments takes place.

In yet another embodiment, the membrane divides non-vascular cells from cells comprising a vascular network. Each side is referred to herein as a "compartment." Non-vascular cell types can include parenchymal cells. Parenchymal cells include, but are not limited to smooth or skeletal muscle cells, myocytes, fibroblasts, chondrocytes, adipocytes, fibromyoblasts, ectodermal cells, including ductile and skin cells, liver cells (e.g., hepatocytes, kupffer cells), kidney cells, pancreatic islet cells, cells present in the intestine, nerve cells, osteoblasts and other cells forming bone or cartilage, and hematopoietic cells (e.g., mast cells).

In yet another embodiment, the compartments of a channel can be interconnected within a single layer by structures comprising bridges. Bridges between compartments connect one section of a compartment to another compartment or another section of the same compartment, within a single layer. Bridges can connect compartments having same cell types, or compatible cell types. Compatible cell types are those which provide support for primary cell types (e.g., organ specific cell types), such as stromal or connective cell types. Heterotypic interactions between fibroblasts and hepatocytes have been shown to be critical for hepatocyte viability, and therefore, these cells are an example of compatible cell types.

In yet another embodiment, three-dimensional systems of the invention comprise a device. The device can be extracorporeal or implantable. Specific applications include use of the device as a biodegradable scaffold in methods of tissue engineering; use as a biodegradable or biologically compatible life assist; use as a biohybrid artificial organ or tissue; and use in drug delivery.

Thus, the invention provides scalable techniques for producing organs, or portions thereof, large enough to transplant into a subject, such as animal recipients, typically vertebrate recipients, and preferably human recipients. A "subject" is a vertebrate, preferably a mammal, and most preferably a human. Mammals include, but are not limited to, humans, farm animals, sport animals, and pets (e.g., dogs, cats). One of skill in the art can readily vary the parameters of the methods described herein to accommodate hosts or subjects of variable size and species, including but not limited to, humans of any age.

In yet another embodiment, the three-dimensional systems of the invention can be used to carry out pharmacological studies of candidate drugs, to test for toxicity and efficacy of lead compounds or existing drugs, to replace suspect animal models and expensive clinical trials.

As used herein, the terms "comprises", "comprising", and the like can have the meaning ascribed to them in U.S. Patent Law and can mean "includes", "including" and the like.

These and other embodiments are disclosed or are obvious from and encompassed by, the following Detailed Description.

BRIEF DESCRIPTION OF THE FIGURES

The following Detailed Description, given by way of example, but not intended to limit the invention to specific embodiments described, may be understood in conjunction with the accompanying Figures, incorporated herein by reference, in which:

FIG. 18 A) shows that pores and channels are maintained during the bonding process. FIG. 18 B) shows pores out of focus, while channels are in focus. Pores become more difficult to detect after bonding. They are clearest when the rest of the design features are out of focus.

DETAILED DESCRIPTION OF THE INVENTION

Figure 1:
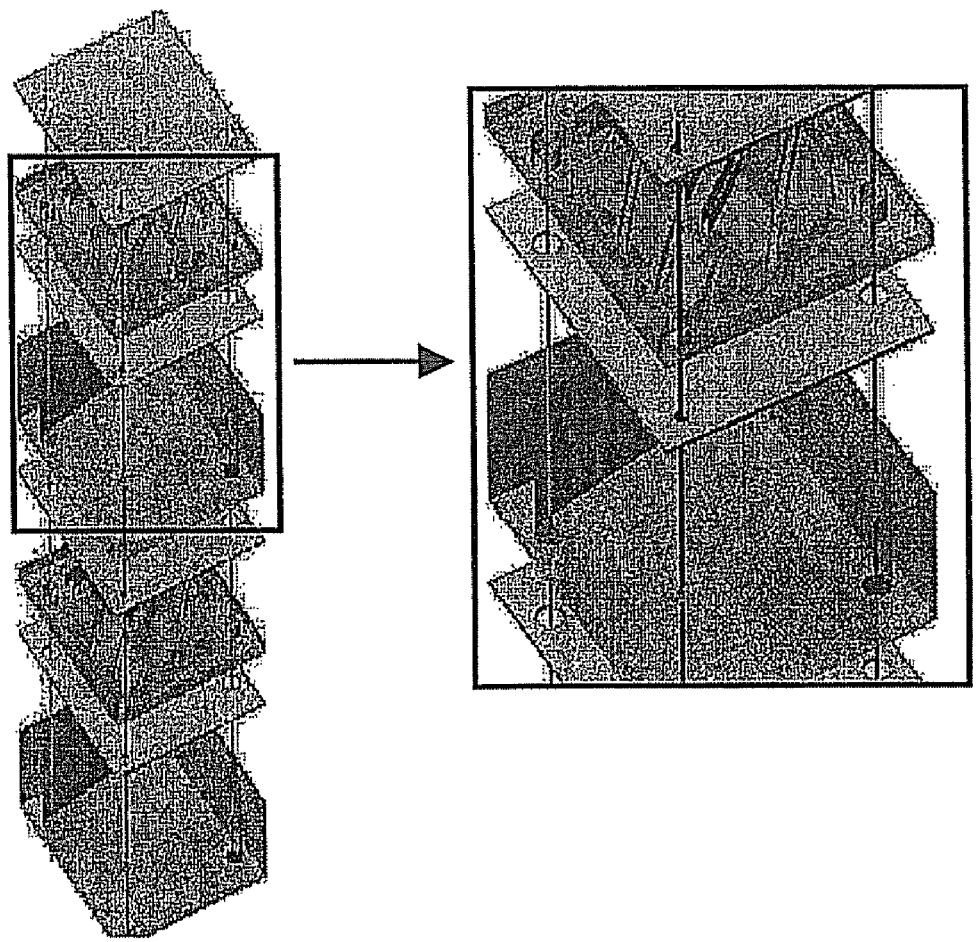
FIG. 1 depicts a schematic of a former method for generating engineered tissues using co-culture. The rose-colored layer represents vascular endothelial cell channels, which are separated from the semi-transparent block containing organ-specific cells by the gray semi-permeable membrane. Cell placement is achieved by separating channel networks for each cell type and filling them sequentially and separately.
Figure 2:
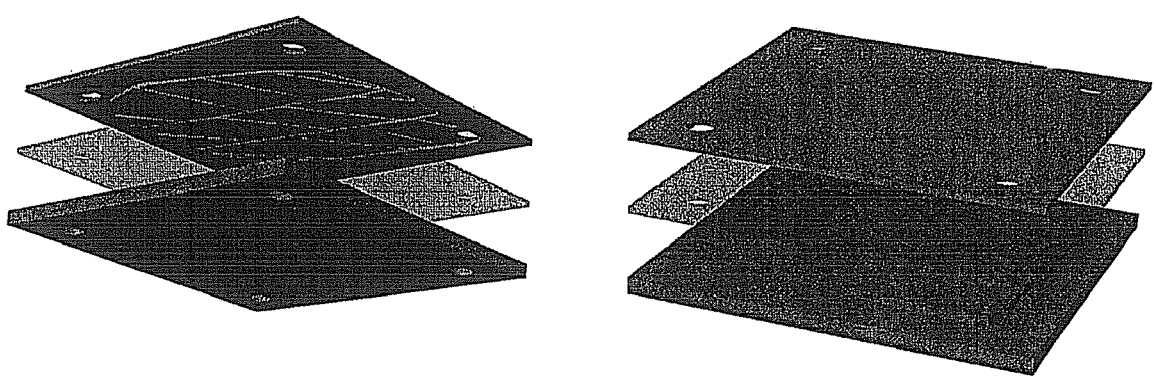
FIG. 2 depicts an alternate view of the former method for producing tissue-engineered constructs using stacking of interspersed layers of parenchymal cells, membranes and vascular cells.

The present invention provides a three-dimensional system comprising at least two layers, wherein each layer comprises channels divided longitudinally into two compartments by a centrally positioned membrane. Each compartment can comprise a different cell type (e.g., organ-specific cells in one compartment and a vascular supply in the second compartment). As a result, an aggregate of cell types can be contained in a single layer, which is then integrated into a multi-layer system.

Each layer of the system will have a support element, comprising a surface in which the channels are formed. The support element can be made of f nondegradable polymers such as PolyDiMethylSiloxane (PDMS), PolyMethylMethacrylate (PMMA), or can comprise biodegradable materials such as PolyCaproLactone (PCL), or biorubber, but the invention is not so limited.

The support element can comprise a mold. A two-dimensional (x, y) mold is fabricated using high-resolution molding processes, such as micromachined wafer technology, thick photoresist processes, or other techniques, to create a patterned of micromachined, small dimensioned channels ("microchannels"), such that the micromachined channels are connected for the circulation of fluid in the multilayer apparatus. Microchannels can comprise, for example, open-faced channels defined by walls extending from a tissue-defining surface into a substrate. The invention also encompasses a substrate wherein the tissue-defining surface comprises an open-faced compartment defined by walls extending from a tissue-defining surface into a substrate.

Manufacture of Molds and Polymer Scaffolds

Each layer of the system will have a support element that can comprise a mold. For purposes of this invention a "mold" is a device on the surface of which the branching structure of the microchannels is etched or formed. Fabrication of a mold begins by selection of an appropriate substrate. The choice of a substrate material is guided by many considerations, including the requirements placed on the fabrication process by the desired mold dimensions, the desired size of the ultimate template, and the surface properties of the wafer and their interaction with the various cell types, extracellular matrix ("ECM") and polymeric backbone. Also important are the thermal properties, such as the glass transition temperature (Tg), which must be high enough so that the network of pores in the mold does not collapse upon solvent removal if a thermal process is used to process the layers.

Molds of the present invention can comprise a variety of materials, including, but not limited to, inert materials such as silicon, polymers such as polyethylene vinyl acetate, polycarbonate, and polypropylene, and materials such as a ceramic or material such as hydroxyapatite. In particular, the mold can comprise from metals, ceramics, semiconductors, organics, polymers, and composites. Representative metals and semiconductors include pharmaceutical grade stainless steel, gold, titanium, nickel, iron, gold, tin, chromium, copper, alloys of these or other metals, silicon, silicon dioxide. These materials are either inherently suitable for the attachment and culture of animal cells or can be made suitable by coating with materials described herein to enhance cell attachment and culture (e.g. gelatin, matrigel, vitrogen and other tissue culture coatings known in the art).

MEMS replica molding can be used to make a "polymer scaffold" for seeding cells. In this method, a mold is made as described herein, preferably of silicon, and is then used as a template on which a polymeric material is cast. Optionally, the polymer scaffold can then be peeled away from the mold and seeded with cells.

A "tissue-defining surface" is the surface of a mold or a polymer scaffold, and a "substrate" is the mold or polymer scaffold itself.

The term "polymer" includes polymers and monomers that can be polymerized or adhered to form an integral unit. The polymer can be non-biodegradable or biodegradable, typically via hydrolysis or enzymatic cleavage. Biodegradable matrices are not typically preferred to construct molds, since they are not implanted and are preferably reusable. For implantation, polymer scaffolds are preferably used, more preferably biodegradable polymer scaffolds.

Preferably, the biodegradable polymer scaffold comprises biodegradable elastomers formed from hydrolyzable monomers as described in Wang et al, Nature Biotech 20, 602 (2002), the contents of which are incorporated herein by reference. These biodegradable elastomers are analogous to vulcanized rubber in that crosslinks in a three-dimensional network of random coils are formed. These biodegradable elastomers are hydrolyzed over time, preferably within 60 days.

Polymer material for implantation should be selected for biocompatibility. Any degradation products should also be biologically compatible. Relatively high rigidity is advantageous so that the polymer scaffold can withstand the contractile forces exerted by cells growing within the mold. A biologically compatible degradable polymer and its degradation products are non-toxic toward the recipient.

The term "biodegradable" refers to materials that are bioresorbable and/or degrade and/or break down by mechanical degradation upon interaction with a physiological environment into components that are metabolizable or excretable, over a period of time from minutes to three years, preferably less than one year, while maintaining the requisite structural integrity. As used in reference to polymers, the term "degrade" refers to cleavage of the polymer chain, such that the molecular weight stays approximately constant at the oligomer level and particles of polymer remain following degradation.

The term "completely degrade" refers to cleavage of the polymer at the molecular level such that there is essentially complete loss of mass. The term "degrade" as used herein includes "completely degrade" unless otherwise indicated.

Materials suitable for polymer scaffold fabrication include, but are not limited to, poly-dimethyl-siloxane (PDMS), polyglycerol-sebacate (PGS), polylactic acid (PLA), poly-L-lactic acid (PLLA), poly-D-lactic acid (PDLA), polyglycolide, polyglycolic acid (PGA), polylactide-co-glycolide (PLGA), polydioxanone, polygluconate, polylactic acid-polyethylene oxide copolymers, modified cellulose, collagen, polyhydroxybutyrate, polyhydroxpriopionic acid, polyphosphoester, poly (alpha-hydroxy acid), polycaprolactone, polycarbonates, polyamides, polyanhydrides, polyamino acids, polyorthoesters, polyacetals, polycyanoacrylates, degradable urethanes, aliphatic polyesterspolyacrylates, polymethacrylate, acyl substituted cellulose acetates, non-degradable polyurethanes, polystyrenes, polyvinyl chloride, polyvinyl flouride, polyvinyl imidazole, chlorosulphonated polyolifins, polyethylene oxide, polyvinyl alcohol, Teflon®, nylon silicon, and shape memory materials, such as poly (styreneblock-butadiene), polynorbornene, hydrogels, metallic alloys, and oligo (s-caprolactone) diol as switching segment/ oligo (p-dioxyanone) diol as physical crosslink. Other suitable polymers can be obtained by reference to The Polymer Handbook, 3rd edition (Wiley, N.Y., 1989). Combinations of these polymers may also be used.

Polylactide-co-glycolides (PLGA), as well as polylactides (PLA) and polyglycolides (PGA) have been used to make biodegradable implants for drug delivery. See U.S. Pat. Nos. 6,183,781 and 6,733,767 and references cited therein, the contents of which are specifically incorporated herein by reference. The ratio of lactide to glycolide of the poly (lactide-co-glycolide) copolymer can be, for example, 75:25, 60:40, 85:15 or 65:35. Biodegradable materials have been developed for use as implantable prostheses, as pastes, and as templates around which the body can regenerate various types of tissue. Polymers that are both biologically compatible and resorbable in vivo are known in the art as alternatives to autogenic or allogenic substitutes. In a preferred embodiment, polymers are selected based on the ability of the polymer to elicit the appropriate biological response from cells, for example, attachment, migration, proliferation and gene expression.

Solvents for most of the thermoplastic polymers are known, for example, methylene chloride or other organic solvents. Organic and aqueous solvents for protein and polysaccharide polymers are also known. The binder can be the same material as is used in conventional powder processing methods or can be designed to ultimately yield the same binder through chemical or physical changes that occur as a result of heating, photopolymerization, or catalysis.

Properties of the mold and/or polymer scaffold surface can be manipulated through the inclusion of materials on the mold or in polymer scaffold material which alter cell attachment (for example, by altering the surface charge or structure), porosity, flexibility or rigidity (which may be desirable to facilitate removal of tissue constructs). Moreover, advances in polymer chemistry can aid in the mechanical tasks of lifting and folding as well as the biologic tasks of adhesion and gene expression. A "release layer" can be deposited onto the molds. The release layer can comprise materials such as, but not limited to, teflon-like layers generated by C4F8 plasma treatment. The release layer can be deposited in solid, liquid or vapor phase. Its main function is to reduce adhesion of the polymer replica to the master mold.

For example, molds can be coated with a unique temperature-responsive polymer, poly-N-isopropyl acrylamide (PNIPAAm), which demonstrates a fully expanded chain conformation below 32° C. and a collapsed, compact conformation at high temperatures. When grafted onto surfaces of silicon wafers using electron beam irradiation, it can be used as a temperature switch for creating hydrophilic surfaces below 32° C. and hydrophobic surfaces above 32° C. Since PNIPAAm is insoluble in water over the lower critical solution temperature (LCST about 32° C.) and reversibly solubilized below the LCST, cells detach from the substratum by simply lowering the temperature below the LCST. One of skill in the art can (1) engraft the polymer on silicon wafers that are pre-coated with polystyrene or (2) engraft the polymer on silicon wafers whose surface is first modified by vinyl-trichlolorosilane. Either of these techniques will ensure that the polymer is better integrated and conjugated to its substratum (polystyrene in the former case and vinyl groups in the later case) so that it can serve as an effective thermal switch, useful in reversing cell attachment and detachment as a single contiguous layer of cells without the usual cell damage.

Another system for promoting both cellular adhesion and lifting of cells as intact sheets can involve the use of RGD (Arg-Gly-Asp) peptides. The RGD sequence is part of the domain within the fibronectin molecule that endows it with the ability to interact with adhesion molecules present on the cell surface of fibroblasts. Fibronectin itself is a well-characterized extracellular, structural glycoprotein which interacts strongly with other extracellular matrix molecules and which causes the attachment and spreading of most cells. This function of the fibronectin molecule is localized primarily to the RGD sequence. One of skill in the art can synthesize RGD peptides with a structural backbone of PMMA that has an RGD peptide sequence at its tips, bound to one another with the intermediate layering of polyethylene oxide. This allows differential cell adhesion in only selected areas and not others. Once the tissue of desired quality is formed, release of this intact monolayer of tissue from its substratum is straightforward; it requires only the addition of soluble RGD to the culture medium to act as a competitive substrate to the insolubilized RGD substrate on the silicon mold surface.

In some embodiments, attachment of the cells to the mold and/or polymer scaffold is enhanced by coating the substrate with compounds such as basement membrane components, agar, agarose, gelatin, gum arabic, types I, II, III, IV, and V collagen, fibronectin, laminin, glycosaminoglycans, matrigel, vitrogen, mixtures thereof, and other materials known to those skilled in the art of cell culture.

Thus, by the methods of the invention, cells can be grown on molds that are uncoated or coated as described herein, depending upon the material used for mold construction. Alternatively, cells can be grown on polymer scaffolds made by replica molding techniques.

Micromachining and Chemical Processing of Silicon and Other Mold Materials

Molds can be made by creating small mechanical structures in silicon, metal, polymer, and other materials using microfabrication processes. These microfabrication processes are based on well-established methods used to make integrated circuits and other microelectronic devices, augmented by additional methods developed by workers in the field of micromachining.

Microfabrication processes that can be used in making the molds disclosed herein include lithography; etching techniques, such as lasers, plasma etching, photolithography, or chemical etching such as wet chemical, dry, and photoresist removal; or by solid free form techniques, including three-dimensional printing (3DP), stereolithography (SLA), selective laser sintering (SLS), ballistic particle manufacturing (BPM) and fusion deposition modeling (FDM); by micromachining; thermal oxidation of silicon; electroplating and electroless plating; diffusion processes, such as boron, phosphorus, arsenic, and antimony diffusion; ion implantation; film deposition, such as evaporation (filament, electron beam, flash, and shadowing and step coverage), sputtering, chemical vapor deposition (CVD), epitaxy (vapor phase, liquid phase, and molecular beam), electroplating, screen printing, lamination or by combinations thereof. See Jaeger, *Introduction to Microelectronic Fabrication* (Addison-Wesley Publishing Co., Reading Mass. 1988); Runyan, et al., Semiconductor Integrated Circuit Processing Technology (Addison-Wesley Publishing Co., Reading Mass. 1990); Proceedings of the IEEE Micro Electro Mechanical Systems Conference 1987-1998; Rai-Choudhury, ed., *Handbook of Microlithography Micromachining & Microfabrication* (SPIE Optical Engineering Press, Bellingham, Wash. 1997). The selection of the material that is used as the mold determines how the surface is configured to form the branching structure. The following methods are preferred for making molds.

Typically, micromachining is performed on standard bulk single crystal silicon wafers of a diameter ranging between about 50 and 300 millimeters (mm), preferably approximately 60 mm, and of thickness ranging between about 200 and 1200 um. These wafers can be obtained from a large number of vendors of standard semiconductor material, and are sawn and polished to provide precise dimensions, uniform crystallographic orientation, and highly polished, optically flat surfaces.

Wafers made from pyrex borosilicate or other glasses can also be procured and inserted into micromachining processes, with alternative processes used to etch the glassy materials.

The geometry of the mold, in particular the number of different feature depths required, is the major factor determining the specific process sequence. The simplest case is that of a single depth dimension for the mold. Specifically, for a silicon substrate, one type of process sequence is as follows: first, the silicon wafer is cleaned, and a layer of photosensitive material is applied to the surface. Typically, the layer is spun on at a high revolution rate to obtain a coating of uniform thickness. The photoresist is baked, and the wafer is then exposed to ultraviolet or other short-wavelength light though a semi-transparent mask. This step can be accomplished using any one of several masking techniques, depending on the desired image resolution. The resist is then developed in appropriate developer chemistry, and the wafer is then hardbaked to remove excess solvent from the resist. Once the lithographic process has been completed, the wafer can be etched in a plasma reactor using one of several possible chemistries. Etching serves to transfer the two-dimensional pattern into the third dimension: a specified depth into the wafer. Plasma parameters are determined by the desired shape of the resulting trench (semi-circular, straight-walled profile, angled sidewall), as well as by the selectivity of the etchant for silicon over the masking photoresist. Once the etching has been completed, the photoresist can be removed and the wafer prepared for use in the tissue molding process.

Increased flexibility in the geometry of wafer mold can be obtained by inserting additional cycles of masking and etching. This modification provides the opportunity to machine channels of varying depths into the wafer mold. To design a mold that is suitable for the culturing of endothelial cells, increased flexibility is very important due to the need for vascular branches with different diameters. The techniques can be extended to provide as many additional layers and different depths as are desired. In addition, these techniques can be used to create secondary patterns within the pattern of microchannels. For example, it may be advantageous to have wells within the microchannels for culturing additional cell types such as feeder cells. The pattern of microchannels also can be designed to control cell growth, for example, to selectively control the differentiation of cells.

Another type of mold is fabricated simply through photolithography with no etching. The standard photoresist for this type of process, known as SU-8, is an epoxy resin negative resist material designed for use in conventional mask aligners. Resin viscosity can be adjusted to provide an enormous range of resultant thicknesses, providing layers as thin as 2 microns but as thick as 1 mm for various applications. Challenges involving film adhesion and cracking can be addressed by suitable process modifications.

One highly advantageous aspect of high aspect ratio photolithography is the ability to produce multiple pattern heights in the film, simply by using multiple exposures followed by a single development step, or other straightforward process variations. Feature geometry, such as the curvature of sidewalls at the top and bottom of structures, can be controlled by varying the baking parameters during processing. Subsequent adhesion of polymer films during replica demolding is often low enough to enable ease of release, but plasma deposition equipment may be used to apply a thin mold release layer as required.

Glass and polymeric wafer molds can be fabricated using a similar sequence, but the actual process can be modified by the addition of an intervening masking layer, since etchants for these materials may attack photoresist as well. Such intervening materials simply function to transfer the pattern from the photoresist to interlayer and then on to the wafer below. For silicon etched in one of several wet chemistries, an intervening layer may also be necessary.

Molds formed of silicon dioxide can be made by oxidizing the surface of the silicon mold forms, rather than depositing a metal and then etching away the solid needle forms to leave the hollow silicon dioxide structures. In one embodiment, hollow, porous, or solid molds are provided with longitudinal grooves or other modifications to the exterior surface of the molds.

Polymeric molds can also be made using microfabrication. For example, the epoxy molds can be made as described above, and injection molding techniques can be applied to form the structures. These micromolding techniques are relatively less expensive to replicate than the other methods described herein.

Three dimensional printing (3DP) is described by Sachs, et al., *Manufacturing Review* 5, 117-126 (1992) and U.S. Pat. No. 5,204,055 to Sachs, et al. 3DP is used to create a solid object by ink-jet printing a binder into selected areas of sequentially deposited layers of powder. Each layer is created by spreading a thin layer of powder over the surface of a powder bed. The powder bed is supported by a piston, which descends upon powder spreading and printing of each layer (or, conversely, the ink jets and spreader are raised after printing of each layer and the bed remains stationary). Instructions for each layer are derived directly from a computer-aided design (CAD) representation of the component. The area to be printed is obtained by computing the area of intersection between the desired plane and the CAD representation of the object. The individual sliced segments or layers are joined to form the three-dimensional structure. The unbound powder supports temporarily unconnected portions of the component as the structure is built but is removed after completion of printing.

SFF methods other than 3DP that can be utilized to some degree as described herein are stereo-lithography (SLA), selective laser sintering (SLS), ballistic particle manufacturing (BPM), and fusion deposition modeling (FDM). SLA is based on the use of a focused ultra-violet (UV) laser that is vector scanned over the top of a bath of a photopolymerizable liquid polymer material. The UV laser causes the bath to polymerize where the laser beam strikes the surface of the bath, resulting in the creation of a first solid plastic layer at and just below the surface. The solid layer is then lowered into the bath and the laser generated polymerization process is repeated for the generation of the next layer, and so on, until a plurality of superimposed layers forming the desired apparatus is obtained. The most recently created layer in each case is always lowered to a position for the creation of the next layer slightly below the surface of the liquid bath. A system for stereolithography is made and sold by 3D Systems, Inc., of Valencia, Calif., which is readily adaptable for use with biologically compatible polymeric materials. SLS also uses a focused laser beam, but to sinter areas of a loosely compacted plastic powder, the powder being applied layer by layer. In this method, a thin layer of powder is spread evenly onto a flat surface with a roller mechanism. The powder is then raster-scanned with a high-power laser beam. The powder material that is struck by the laser beam is fused, while the other areas of powder remain dissociated. Successive layers of powder are deposited and raster-scanned, one on top of another, until an entire part is complete. Each layer is sintered deeply enough to bond it to the preceding layer. A suitable system adaptable for use in making medical devices is available from DTM Corporation of Austin, Tex.

BPM uses an ink-jet printing apparatus wherein an ink-jet stream of liquid polymer or polymer composite material is used to create three-dimensional objects under computer control, similar to the way an ink-jet printer produces two-dimensional graphic printing. The mold is formed by printing successive cross-sections, one layer after another, to a target using a cold welding or rapid solidification technique, which causes bonding between the particles and the successive layers. This approach as applied to metal or metal composites has been proposed by Automated Dynamic Corporation of Troy, N.Y. FDM employs an x-y plotter with a z motion to position an extrudable filament formed of a polymeric material, rendered fluid by heat or the presence of a solvent. A suitable system is available from Stratasys, Incorporated of Minneapolis, Minn.

The design of the channels in the mold can be constructed by a number of means, such as fractal mathematics, which can be converted by computers into two-dimensional arrays of branches and then etched onto wafers. Also, computers can model from live or preserved organ or tissue specimens three-dimensional vascular channels, convert to two-dimensional patterns and then help in the reconversion to a three-dimensional living vascularized structure. Techniques for producing the molds include techniques for fabrication of computer chips and microfabrication technologies. Other technologies include laser techniques.

Design of Apparatus

The present invention provides a three-dimensional system comprising at least two layers, wherein each layer comprises channels divided longitudinally into two compartments by a centrally positioned membrane. Each compartment can comprise a different cell type (e.g., organ-specific cells in one compartment and a vascular supply in the second compartment). As a result, an aggregate of cell types can be contained in a single layer, which is then integrated into a multi-layer system.

Figure 3:
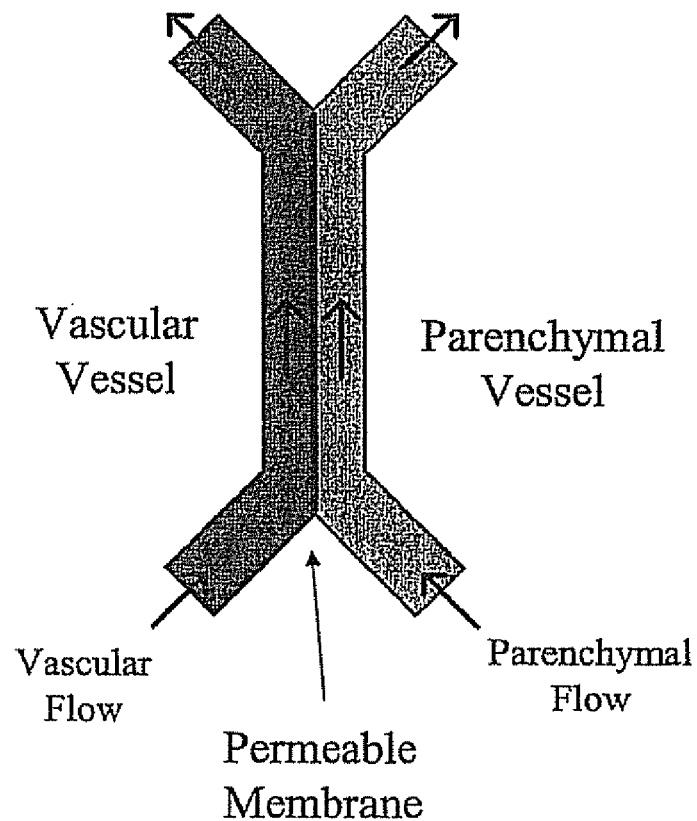
FIG. 3 depicts the simplest subunit of the tissue-engineered system. A porous membrane, all within a single layer, separates a vascular vessel and parenchymal vessel.

A diagram showing the spatial relationship of parenchymal and vascular cells is shown in FIG. 3, where a permeable membrane is depicted, separating the two cell layers in a single channel. The membrane vertically transects the center of each channel, dividing cell types as desired into two compartments. FIG. 3 represents the simplest subunit of a system of the present invention.

Figure 4:
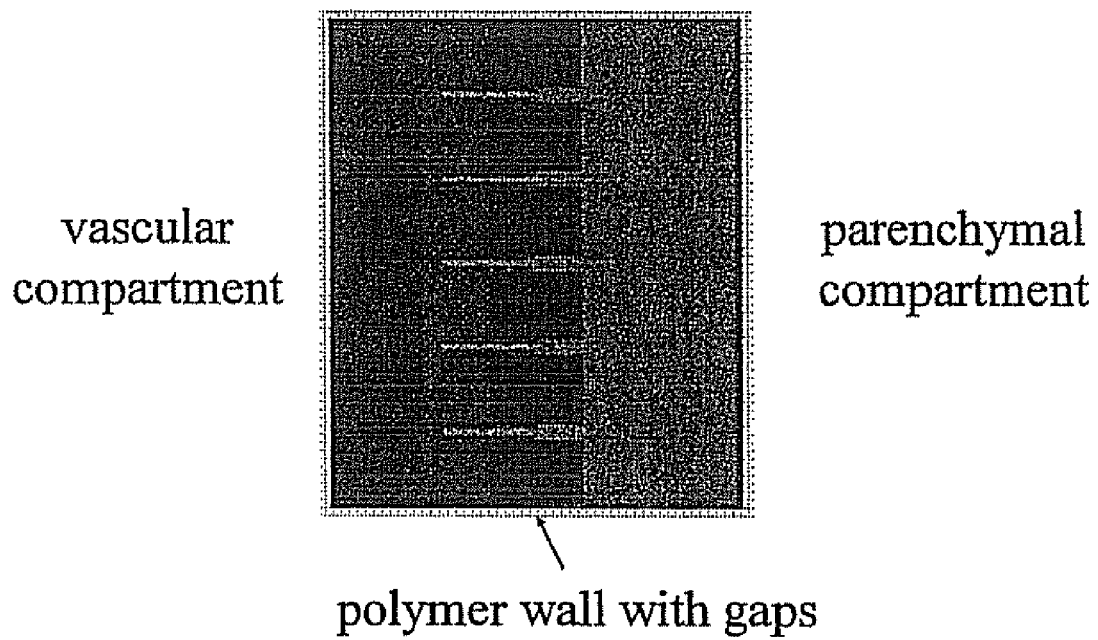
FIG. 4 depicts an overhead view of a membrane created by leaving nano-pore gaps in the wall between the two compartments (arrows denote flow across the membrane).
Figure 5:
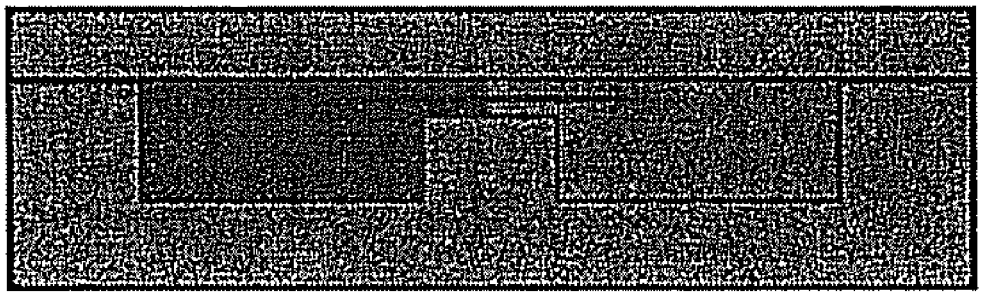
FIG. 5 depicts a cross-sectional view of a nano-scale pore between two compartments (arrow denotes flow across the membrane).

The membrane can comprise a wall of polymer having pores to allow transport from one compartment to the other. The pores can be constructed in at least two ways. Leaving gaps in the polymer wall, as shown in FIG. 4, can create pores on the micron-scale. FIG. 4 represents one embodiment, wherein leaving gaps in the wall between the two compartments can create the membrane. Smaller nano-scale pores in the membrane (e.g., less than 100 nm, 100-200 nm, 200-800 nm) can be created by utilizing the fine control of the wafer fabrication methods in the direction perpendicular to the plane of the wafer. This method creates a membrane as in FIG. 5, which depicts a cross-sectional view of a nano-scale pore between two compartments.

Figure 6:
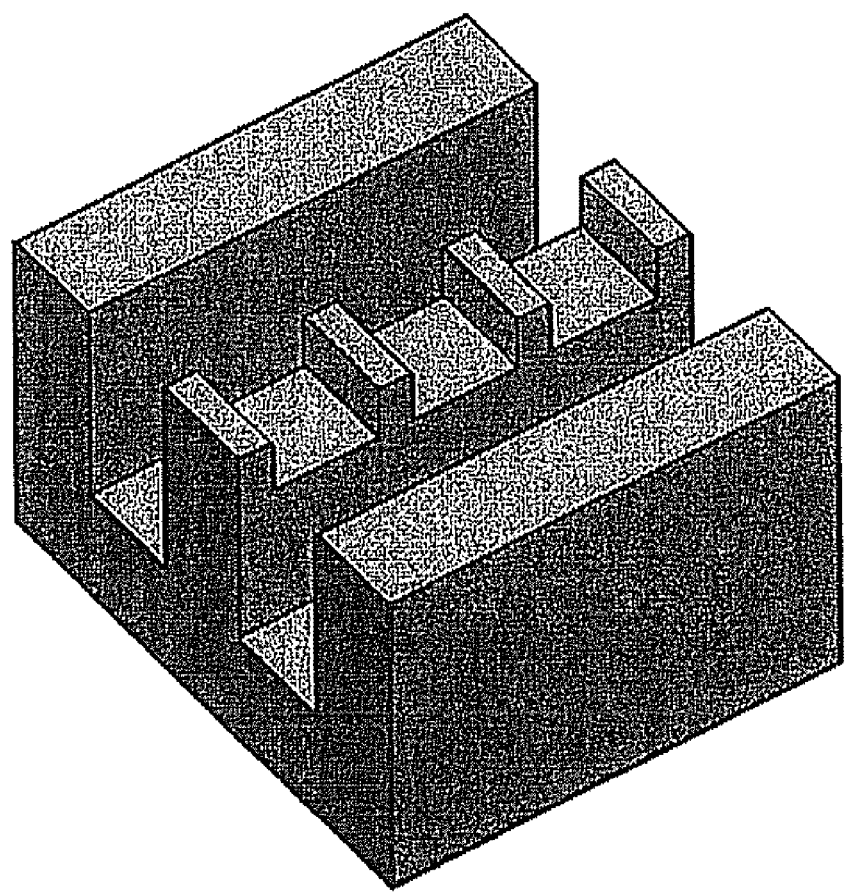
FIG. 6 depicts a cutaway view of a membrane constructed using a combination of nano-scale and micron-scale techniques. Nano-scale techniques allow fine control of channel dimensions while micron-scale techniques add mechanical support posts.

These two approaches for creating channels can be combined, effectively adding posts in the nano-scale gap to increase support. A membrane incorporating both embodiments is shown in FIG. 6, which shows a cutaway view of the membrane constructed using a combination of nano-scale and micron-scale techniques. Nano-scale techniques allow fine control of channel dimensions, while micron-scale techniques add mechanical support posts.

A sealant can be placed over the channels. The sealant can be made of the same or different material used to form the support element.

Figure 7:
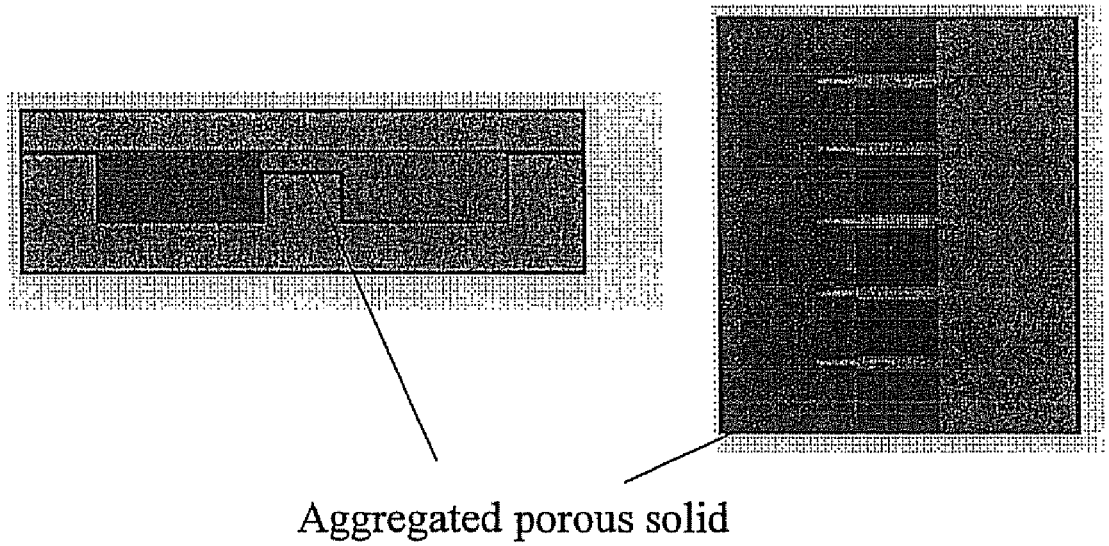
FIG. 7 depicts the addition of acid-solubilized collagen or a self-assembling peptide flowed into network aggregates in mechanical pores to enhance filtration.

Filtration of solutes can be further achieved by addition of an aggregated porous solid to the pores to enhance filtration by restricting the flow of large molecules (FIG. 7). Materials that can be used as aggregated porous solids include, but are not limited to, acid-solubilized collagen or self-assembling peptides. The solid material can incorporate into the membrane, providing additional support, or altering the geometry or transport properties of the pores in a controlled way. The solid material can be a porous solid, including but not limited to, collagen (e.g., Matrigel™), fibronectin, laminin, or self-assembling peptides, but the invention is not so limited. In one embodiment, the solid material can incorporate into the nanopore, to further subdivide the area in which flow between compartments takes place.

Figure 8:
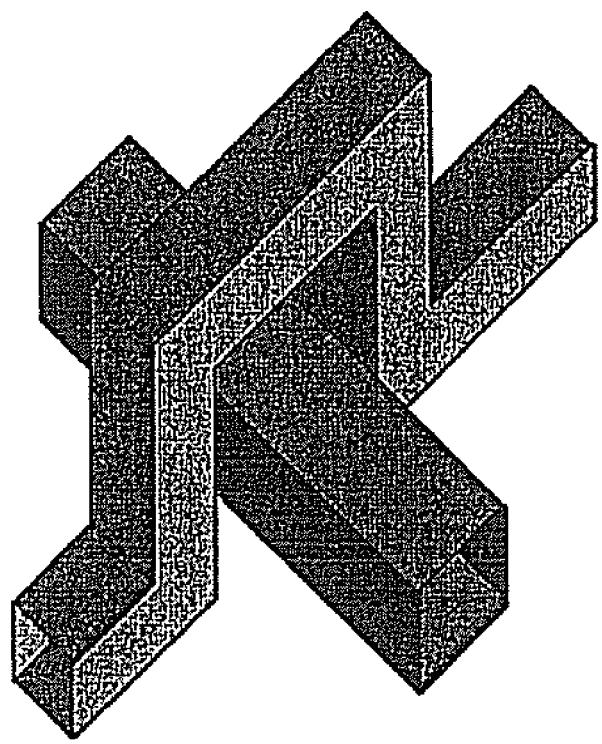
FIG. 8 depicts the parenchymal compartment bridges over the vascular, to be placed at any intersection between the vascular and parenchymal compartments.
Figure 9:
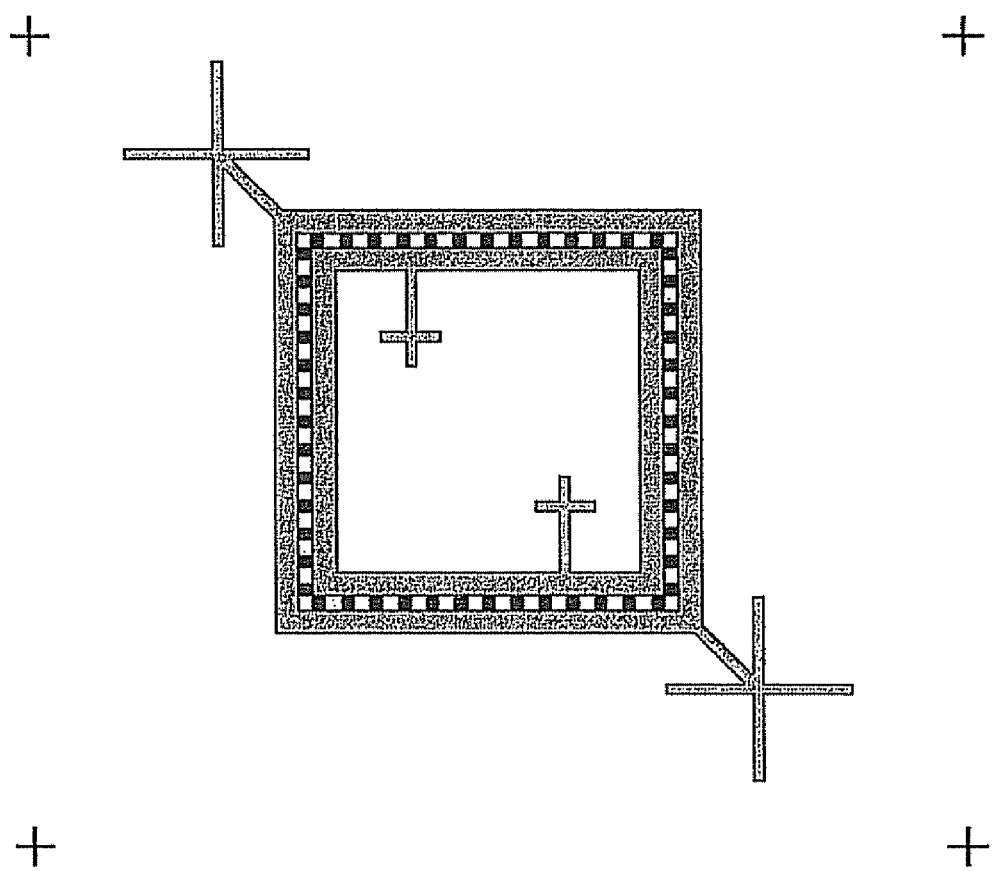
FIG. 9 depicts the bottom layer of the tissue-engineered system. White areas are unetched; gray areas are full-depth etches, and blue areas are nano-scale etches for pores. Crosses connected to network are connection sites for vertical vessels.
Figure 10:
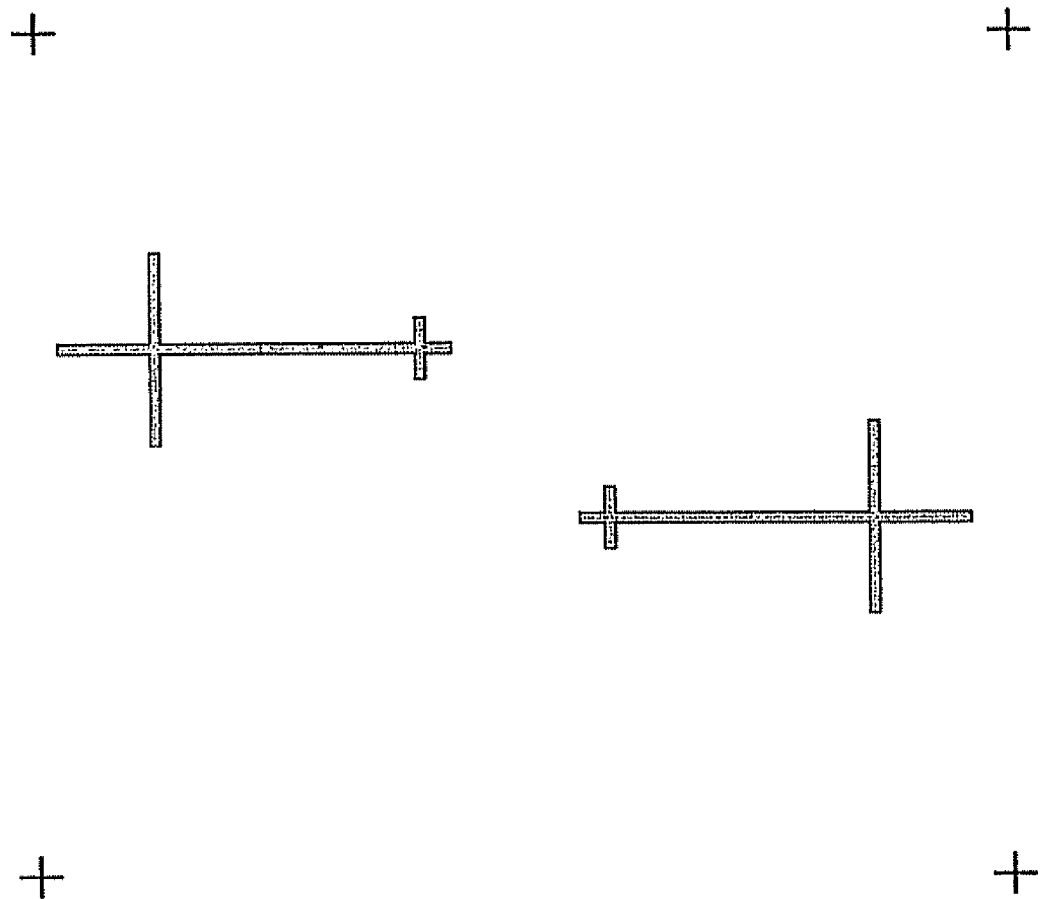
FIG. 10 depicts the upper layer of the tissue-engineered system.
Figure 11:
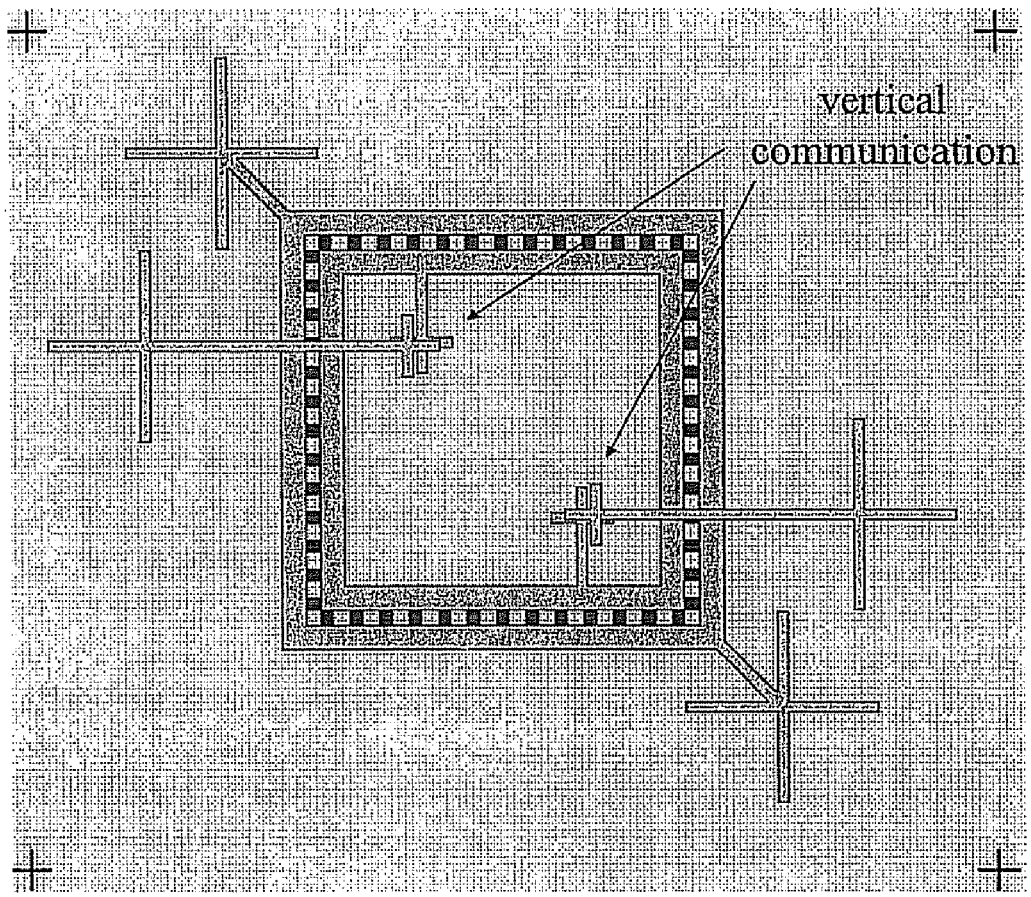
FIG. 11 depicts a complete design, with the upper layer stacked upon the lower layer. Fluid flows between layers via vertical vessels are denoted by arrows.
Figure 12:
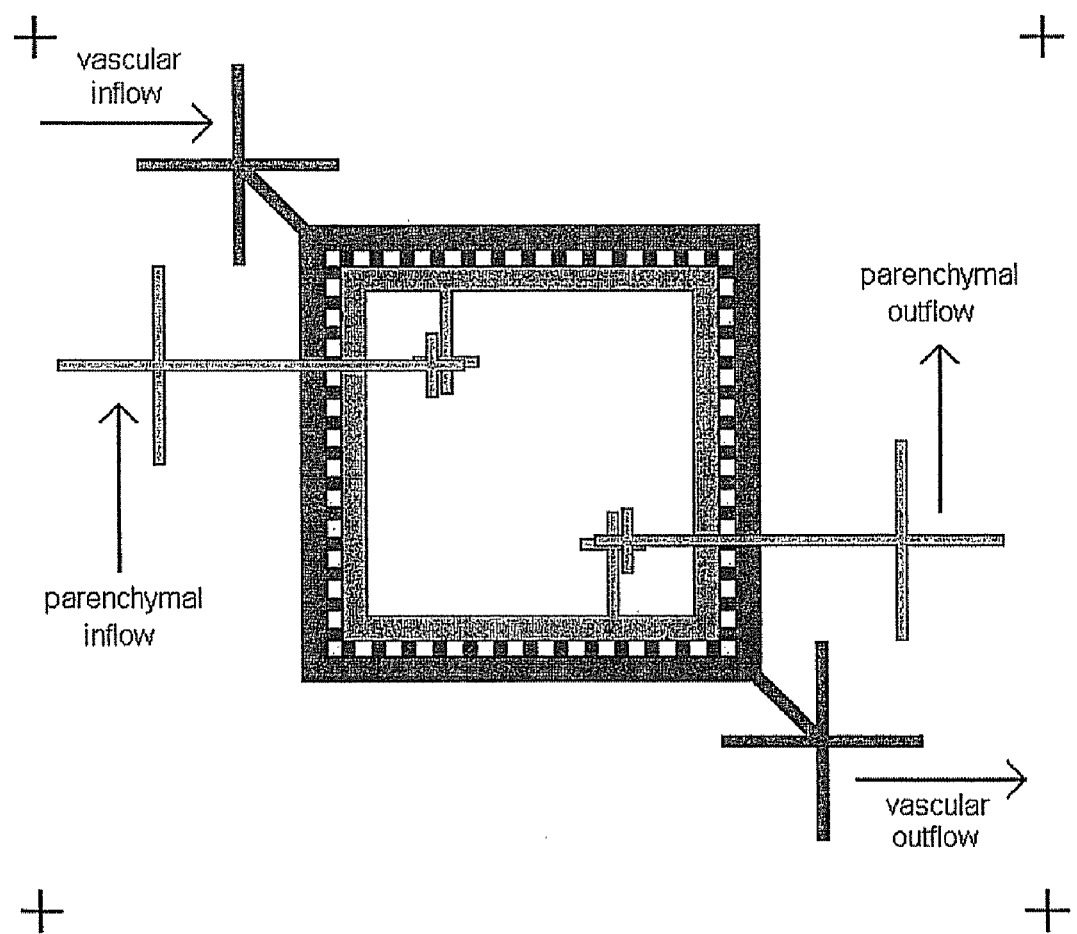
FIG. 12 depicts a flow schematic of the tissue engineered system. The vascular network and porous membrane exist only on the bottom layer. The parenchymal network exists on the upper and lower layer and has vertical interconnects between the two layers.
Figure 13:
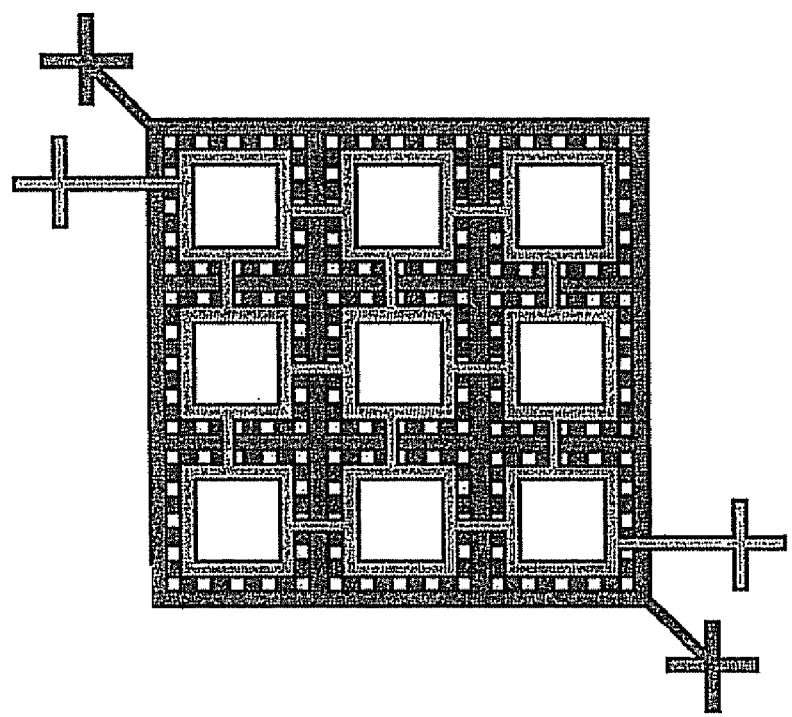
FIG. 13 depicts a tiling pattern used to create large networks. Tiling can extend arbitrarily far in either direction to create networks of any size.
Figure 14:
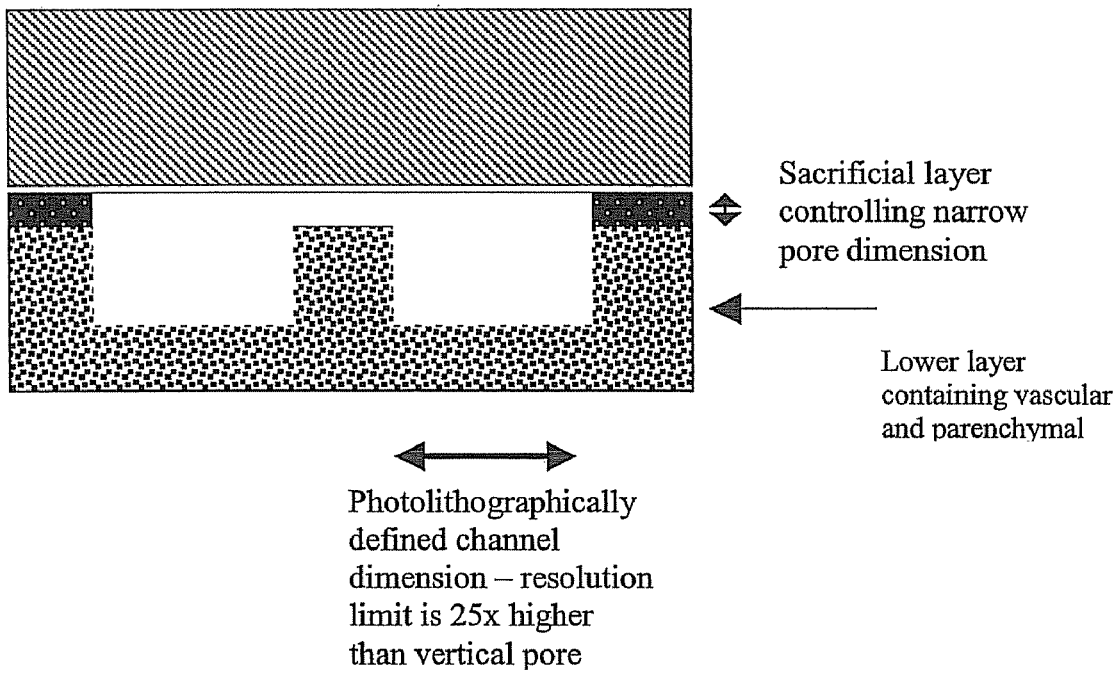
FIG. 14 depicts a schematic illustrating the advantage in resolution obtained by generating pores with the narrow dimension oriented in the z-axis rather than in the plane of the layer.

Numerous subunits can be connected to create complete vascular and parenchymal tissue-engineered network. The compartments can be interconnected within a single layer by structures comprising bridges. The vascular and parenchymal compartments should not intersect, so wherever they cross, the parenchymal compartment can bridge over the vascular compartment, as shown in FIG. 8. Bridges between compartments connect one section of a compartment to another compartment or another section of the same compartment, within a single layer. Bridges may optionally have pores as well. Bridges can connect compartments having same cell types, or compatible cell types. Compatible cell types are those which provide support for primary cell types (e.g., organ specific cell types), such as stromal or connective cell types. For example, fibroblasts provide support hepatocytes, and are therefore a compatible cell type.

Fabrication of a permeable membrane that is integrated within the channels can be carried out using techniques known in the art (Martin et al. (2001) Biomedical Microdevices, 3 (2): 97-108; Leoni et al., (2004) Advanced Drug Delivery Reviews, 56 (2) pp. 211-229). Using these methods, the system is constructed by controlling the thickness of layers in the z-dimension. Typically, nanoscale features (e.g., channels, membrane pores) are constructed by orienting the narrow dimension of the pore along the vertical or z-axis direction. The ability to control the thickness of deposited film is more than an order of magnitude (typically 4 nm) better than control of the width of patterned features. Using these techniques, the mold for the pores is formed by depositing a thin sacrificial layer of controlled thickness on the surface of the mold wafer. Next, the mold for the pores is patterned and machined by photolithography and etching. The etching process is such that a step is created between the mold wafer surface and the height of the sacrificial layer. Finally, channels and other features are etched or lithographically patterned into the mold.

Stacking Molds and/or Polymer Scaffolds to Achieve Three-Dimensionality

Fastening or sealing of the polymeric mold layers is required to be leakproof and support fluid pressures necessary for dynamic cell seeding. Preferably, the layers are irreversibly bound before implantation into the host. Depending on the composition of the layered material, the layers can be sealed by solvent bonding; reflow by heating (40° C.); treating surface with oxygen plasma; or by polymer flow at the surface. Biologically compatible polymer materials maybe bonded together by plasma activation to form sealed structures (Jo et al., SPIE 3877,222 (1999)). The basic process results in bonded layers with channel architecture closely resembling that obtained with silicon etched molds.

One common method used to seal micromachined wafers together is anodic bonding, a technique based on the high concentration of mobile ions in many glasses (Camporese, et al., *IEEE Electron. Device Lett. EDL* 2, 61 (1981)). This process produces a permanent seal; fracture testing of silicon-glass anodically bonded interfaces produces a failure within the bulk of the glass.

Etched wafers may be bonded together, producing closed lumens suitable for fluidic experiments. Alternatively, the multilayered device described by the present invention can be configured such that each of the layers has an alignment indentation on one surface of the layer and an alignment protrusion on the opposing surface of another layer. The alignment indentations can be shaped to mate with the alignment protrusion, so that the layers are held together.

To build up the mold and/or polymer scaffold layers by mechanical assembly, the layers can be mechanically mated using biodegradable or non-biodegradable barbs, pins, screws, clamps, staples, wires, string, or sutures. (See, U.S. Pat. No. 6,143,293.) With this mechanical assembly approach, each prefabricated section can comprise different mold and/or polymer scaffold material and/or different mold microstructures. Different sections of these can be seeded with cells before assembly. Cells thus be can be embedded into the mold or polymer scaffold by assembling sections around these components. In addition, surface features on each mold, which are readily fabricated, become part of the internal microstructure (e.g., molded surface channels become conduits for cell infusion, or for blood flow to stimulate angiogenesis). A surface feature on an individual mold or polymer scaffold will become an internal feature when another segment is assembled over it. For example, surface features such as channels can be micromachined into a first mold or polymer scaffold layer. When a second mold or polymer scaffold layer is placed atop that first layer, the micromachined surface feature becomes an internal feature of the apparatus. Connections between layers are achieved by integrating through-holes alongside the channel-like features in each layer. Through-holes connect in a specified way to the channel network, and connect with through-holes in the layers above and below.

Semi-Permeable Membrane

In the multi-layer systems of the invention, each layer comprises one or more channels having multiple cell types divided longitudinally by a centrally positioned membrane. A semi-permeable membrane can be used to separate the cell types. Preferably, the pore size of the membrane is smaller than the cell diameters, thus, cells will not be able to pass through (i.e. a low permeability for animal cells), while low molecular weight nutrients and fluids can pass through (i.e. a high permeability for nutrients), thereby providing adequate cell-to-cell signaling. Cell sizes vary but in general, they are in the range of microns. For example, a red blood cell has a diameter of 8 m. Preferably, the average membrane pore size is on a submicron-scale to ensure effective screening of the cells.

The membrane can be made of a biologically compatible, nondegradable material such as PolyDiMethylSiloxane (PDMS), PolyMethylMethacrylate (PMMA), PolyEtherSulfone (PES), PolyCarbonate (PC), or from a degradable material such as PLGA, PolyCaproLactone (PCL) or Biorubber, but the invention is not so limited.

Semi-permeable membranes of the present invention comprise a wide array of different membrane types and morphologies, which can be classified as follows:

(1) Track-etched membranes consisting of cylindrical through-holes in a dense polymer matrix. These membranes are typically made by ion-etching; or (2) Fibrous membranes made by various deposition techniques of polymeric fibers. Production methods enable fibrous membranes to have specific molecular weight cut-offs.

Track-etch type membranes are preferred, as they limit the fluid motion in one direction. Preferably, fluid motion is in the vertical direction. Fibrous membranes permit fluid motion both laterally and vertically.

The development of an appropriate membrane will mirror the device progression. Biologically compatible and non-degradable membranes can be incorporated in microchannels that are made from poly (dimethyl siloxane) (PDMS). Since PDMS is non-degradable, the membranes do not need to be degradable either. However, degradable membranes and materials for microchannels can also be used. There exists a variety of commercial track-etched membranes with well-defined pore sizes that can be used for this purpose. Care must be taken to properly incorporate the membranes into the existing microchannels without leaking. To this end, the membranes can be bonded with either an oxygen plasma or a silicone-based adhesive.

A small recession can be designed into the microchannels so that the membrane can fit tightly therein.

In principle, membrane formation from polymers relies on phase-phase separation. Polymer-solvent interactions are complex, and polymer phase diagrams are significantly more complicated than those for monomeric materials, e.g., metals. Phase separation can be induced either by diffusion (diffusion-induced phase separation or "DIPS") or by thermal means (thermal induced phase separation or "TIPS").

A DIPS system comprises polymer, solvent and non-solvent. The polymer solution is cast as a thin film and then immersed in a coagulation bath containing the non-solvent. This process is governed by the diffusion of various low molecular weight components. The exchange of solvent and non-solvent between the polymer solution and the coagulation bath leads to a change in the composition in the film and phase separation is induced. After some time, the composition of the polymer-rich phase reaches the glass transition composition and the system solidifies. To avoid macrovoid formation, a small amount of non-solvent can be mixed with the polymer solution. In a preferred embodiment, the polymer is polycaprolactone (PCL) and the separation system is chloroform/methanol. Specifically, a polymer solution with a concentration ranging from about 5-10% wt. is made. PCL is prepared by dissolving it in chloroform at room temperature under gentle stirring. Once the polymer has completely dissolved, a small amount is placed on a clean mirror surface, and a membrane knife is used to spread out a film with preset thickness. The thickness of the film can be adjusted by changing the gap between the knife blade and the minor surface. Once the film has been spread, the entire mirror is immersed in a methanol bath. Phase separation occurs almost instantaneously, but the film and minor are left in the coagulation bath for up to about 10 minutes to lock in the morphology. A typical membrane thickness is about 100 J. m, and the pore size is on the order of about 1 (J, in, preferably between about 0.01 and 20 um. Membrane morphology can be varied by altering the composition/concentration of the polymer solution, the film thickness, the components of the coagulation bath, and/or the process conditions. One skilled in the art would understand how to vary any one of these parameters to achieve the desired result.

A TIPS system comprises a thermal gradient to induce phase separation. By choosing a polymer-solvent system that is miscible at high temperatures, but immiscible at low temperatures, e.g., room temperature, phase separation can be induced upon cooling down the polymer solution. In a preferred embodiment, the polymer is PCL and the separation system is DMF/10% C3HgO3.

Cells to be Seeded onto the Mold or Polymer Scaffold

Within a single layer of the system, each channel will be divided into two compartments, with the functional cells located in one compartment, and the vasculature located in the other compartment. The compartments of the channel are divided by the membrane. Compartments of the channels within each layer typically include one or more types of functional, mesenchymal or parenchymal cells, such as smooth or skeletal muscle cells, myocytes (muscle stem cells), fibroblasts, chondrocytes, adipocytes, fibromyoblasts, ectodermal cells, including ductile and skin cells, hepatocytes, kidney cells, pancreatic islet cells, cells present in the intestine, and other parenchymal cells, osteoblasts and other cells forming bone or cartilage, and hematopoietic cells. In some cases it may also be desirable to include nerve cells. "Parenchymal cells" include the functional elements of an organ (e.g., organ-specific cells), as distinguished from the framework or stroma. "Mesenchymal cells" include connective and supporting tissues, smooth muscle, vascular endothelium and blood cells.

The membrane dividing the cells allows gas exchange, diffusion of nutrients, and waste removal. Thus, one compartment comprises the circulation through which blood, plasma or media with appropriate levels of oxygen can be continuously circulated to nourish the second compartment. The second compartment comprises a reservoir for functional cells of one or more organs. The system optionally includes inlets for neural inervation, urine flow, biliary excretion or other activity.

Cells can be obtained by biopsy or harvest from a living donor, cell culture, or autopsy, all techniques well known in the art. Cells are preferably autologous. Cells to be implanted can be dissociated using standard techniques such as digestion with a collagenase, trypsin or other protease solution and are then seeded into the mold or polymer scaffold immediately or after being maintained in culture. Cells can be normal or genetically engineered to provide additional or normal function. Immunologically inert cells, such as embryonic or fetal cells, stem cells, and cells genetically engineered to avoid the need for immunosuppression can also be used. Methods and drugs for immunosuppression are known to those skilled in the art of transplantation.

Molecules such as growth factors or hormones can be covalently attached to the surface of the molds and/or polymer scaffolds and/or semi-permeable membrane to effect growth, division, differentiation or maturation of cells cultured thereon.

Preferably, hepatocytes can be used with this invention. The hepatocytes can be highly proliferative hepatocytes, known as small hepatocytes (SHCs), which have the ability to proliferate in vitro for long periods of time (Mitaka, et al., *Biochem Biophys Res Commun* 214, 310 (1995); Taneto, et al., *Am J Pathol* 148, 383 (1996)). Small hepatocytes express hepatocyte specific functions such as albumin production (Mitaka, et al., *Hepatology* 29, 111 (1999)).

Undifferentiated or partially differentiated precursor cells, such as embryonic germ cells (Gearhart, et al., U.S. Pat. No. 6,245,566), embryonic stem cells (Thomson, U.S. Pat. Nos. 5,843,780 and 6,200,802), mesenchymal stem cells (Caplan, et al. U.S. Pat. No. 5,486,359), neural stem cells (Anderson, et al., U.S. Pat. No. 5,849,553), hematopoietic stem cells (Tsukamoto, U.S. Pat. No. 5,061,620), multipotent adult stein cells (Furcht, et al., WO 01/11011) can be used in this invention. Cells can be kept in an undifferentiated state by co-culture with a fibroblast feeder layer (Thomson, U.S. Pat. Nos. 5,843,780 and 6,200,802), or by feeder-free culture with fibroblast conditioned media (Xu, et al. *Nat. Biotechnol.*, 19, 971 (2001)). Undifferentiated or partially differentiated precursor cells can be induced down a particular developmental pathway by culture in medium containing growth factors or other cell-type specific induction factors or agents known in the art. Some examples of such factors are shown in Table 1.

TABLE 1

Selected Examples of Differentiation Inducing Agents

| Agent | Progenitor | Differentiated Cell |
|---|---|---|
| Vascular Endothelial Growth Factor | Embryonic Stem Cell | Hematopoietic Cell[1] |
| Sonic Hedgehog | Floor Plate | Motor Neuron[2] |
| Insulin-like Growth Factor II | Embryonic Stem Cell | Myoblast[3] |
| Osteogenin | Osteoprogenitor | Osteoblast[4] |
| Cytotoxic T Cell Differentiation Factor | Spleen Cell | Cytotoxic T Lymyphocyte[5] |
| β-catenin | Skin Stem Cell | Follicular Keratinocyte[6] |
| Bone Morphogenic Protein 2 | Mesenchymal Stem Cell | Adipocytes, Osteoblasts[7] |
| Interleukin 2 | Bone Marrow Precursor | Natural Killer Cells[8] |
| Transforming Growth Factor □ | Cardiac Fibroblast | Cardiac Myocyte[9] |
| Nerve Growth Factor | Chromaffin Cell | Sympathetic Neuron[10] |
| Steel Factor | Neural Crest | Melanocyte[11] |
| Interleukin 1 | Mesencephalic Progenitor | Dopaminergic Neuron[12] |
| Fibroblast Growth Factor 2 | GHFT | Lactotrope[13] |
| Retinoic Acid | Promyelocytic Leukemia | Granulocyte[14] |
| Wnt3 | Embryonic Stem Cell | Hematopoietic Cell[15] |

[1]Keller, et al. (1999) *Exp. Hematol.* 27: 777-787.
[2]Marti, et al. (1995) *Nature*. 375: 322-325.
[3]Prelle, et al. (2000) *Biochem. Biophy. Res. Commun.* 277: 631-638.
[4]Amedee, et al. (1994) *Differentiation*. 58: 157-164.
[5]Hardt, et al. (1985) *Eur. J. Immunol.* 15: 472-478.
[6]Huelsken, et al. (2001) *Cell*. 105: 533-545.
[7]Ji, et al. (2000) *J. Bone Miner. Metab*. 18: 132-139.
[8]Migliorati, et al. (1987) *J Immunol*. 138: 3618-3625.
[9]Eghbali, et al. (1991) *Proc. Natl. Acad. Sci. USA*. 88: 795-799.
[10]Niijima, et al. (1995) *J. Neurosci*. 15: 1180-1194.
[11]Guo, et al. (1997) *Dev. Biol*. 184: 61-69.
[12]Ling, et al. (1998) *Exp. Neurol*. 149: 411-423.
[13]Lopez-Fernandez, et al. (2000) *J. Biol. Chem*. 275: 21653-60.
[14]Wang, et al. (1989) *Leuk. Res*. 13: 1091-1097.
[15]Lako, et al. (2001) *Mech. Dev*. 103: 49-59.

A stem cell can be any known in the art, including, but not limited to, embryonic stem cells, adult stein cells, neural stem cells, muscle stem cells, hematopoietic stem cells, mesenchymal stem cells, peripheral blood stem cells and cardiac stem cells. Preferably, the stem cell is human. A "stem cell" is a pluripotent, multipotent or totipotent cell that can undergo self-renewing cell division to give rise to phenotypically and genotypically identical daughter cells for an indefinite time and can ultimately differentiate into at least one final cell type.

The quintessential stem cell is the embryonic stem cell (ES), as it has unlimited self-renewal and multipotent and/or pluripotent differentiation potential, thus possessing the capability of developing into any organ, tissue type or cell type. These cells can be derived from the inner cell mass of the blastocyst, or can be derived from the primordial germ cells from a post-implantation embryo (embryonal germ cells or EG cells). ES and EG cells have been derived from mice, and more recently also from non-human primates and humans. Evans et al. (1981) Nature 292: 154-156; Matsui et al. (1991) Nature 353: 750-2; Thomson et al. (1995) Proc. Natl. Acad. Sci. USA. 92: 7844-8; Thomson et al. (1998) Science 282: 1145-1147; and Shamblott et al. (1998) Proc. Natl. Acad. Sci. USA 95: 13726-31.

The terms "stem cells," "embryonic stein cells," "adult stem cells," "progenitor cells" and "progenitor cell populations" are to be understood as meaning in accordance with the present invention cells that can be derived from any source of adult tissue or organ and can replicate as undifferentiated or lineage committed cells and have the potential to differentiate into at least one, preferably multiple, cell lineages.

Methods for Seeding Cells into Molds or Polymer Scaffolds

After the mold with the desired high degree of micromachining is prepared, the molds themselves or polymer scaffolds are seeded with the desired cells or sets of cells. The distribution of cells throughout the mold or polymer scaffold can influence both (1) the development of a vascularized network, and (2) the successful integration of the vascular device with the host. The approach used in this invention is to provide a mechanism for the ordered distribution of cells onto the mold or polymer scaffold. Cells that are enriched for extracellular matrix molecules or for peptides that enhance cell adhesion can be used. Cells can be seeded onto the mold or polymer scaffold in an ordered manner using methods known in the art, for example, Teebken, et al., *Eur J. Vasa Endovasc. Surg.* 19, 381 (2000); Ranucci, et al., *Biomaterials* 21, 783 (2000). Also, tissue-engineered devices can be improved by seeding cells throughout the polymeric scaffolds and allowing the cells to proliferate in vitro for a predetermined amount of time before implantation, using the methods of Burg et al., *J. Biomed. Mater. Res* 51, 642 (2000).

Seeding of each cell type is done by providing cells to each compartment separately using microfluidic techniques. For example, endothelial cells are introduced into the inlet of the vascular network, and prevented from crossing over to a parenchymal compartment by virtue of the small pores connecting the compartments. Other compartments are filled by the same means, keeping cell types in the desired locations.

In one embodiment, the mold or polymer scaffold is first seeded with a layer of parenchymal cells, such as hepatocytes or renal cells (e.g., proximal tubule cells). This layer can be maintained in culture for a week or so in order to obtain a population doubling. It can be maintained in a perfusion bioreactor to ensure adequate oxygen supply to the cells in the interior. The system is then seeded with a layer of endothelial cells and cultured further. In regions where the matrix is resorbed rapidly, the tissue can expand and become permeated with capillaries.

Cell Seeding of Horizontal Layer by Laminar Flow

Sets of cells can be added to or seeded onto a mold, which can serve as a template for cell adhesion and growth by the added or seeded cells. The added or seeded cells can be parenchymal cells, such as hepatocytes or proximal tubule cells.

Stem cells can also be used. A second set of cells, such as endothelial cells, can be added to or seeded onto the layers of the system through other vessels than those used to seed the first set of cells. The cell seeding is performed by slow flow. As a practical matter, the geometry of the system will determine the flow rates. In general, endothelial cells can enter and form vessel walls in micromachined channels that are about 10-50 µm. Thus, in addition to serving as a mechanical framework for the organ, the assembled system provides a template for all of the microstructural complexity of the organ, so that cells have a mechanical map to locate themselves and form subsystems, such as blood vessels in the liver.

Channels in the horizontal direction typically proceed from larger to smaller to larger. The geometries can be as complex as desired in-plane (horizontal direction). Thus, one can use small geometries in-plane (such as horizontal conduits of about 5-20 µm). The alignment of through-holes creates vertical conduits or channels in the z-axis. However, the vertical channels need not go from larger to smaller to larger. In the vertical direction, the vertical channels are typically parallel to each other and have diameters on the micron level, large enough only to allow cell seeding (e.g., hepatocytes are about 40 µm). In one embodiment, different types of cells are seeded horizontally onto different layers of the assembled apparatus. In another embodiment, the different types of cells are seeded using pores or channels from different directions. Various combinations are also possible.

Extracorporeal Support Devices

The invention can be adapted to comprise devices for uses in addition to the formation of implantable tissue. The devices can be implantable. Alternatively, the systems can remain ex vivo, serving as extracorporeal devices to supplement or replace biological function. As used herein, the term "biological function" refers to the structural, mechanical or metabolic activity of a tissue or organ. Extracorporeal devices of the present invention can comprise hybrid devices suitable for both ex vivo and in vivo use.

Extracorporeal devices, and may provide partial support function, may extend the time between hospital treatments for patients on chronic organ support therapies, and will improve the quality of life between hospital treatments. For example, the device can be adapted to produce an extracorporeal renal dialysis device, an extracorporeal liver device, or an extracorporeal artificial lung device. Such devices may or may not be supported with living cells loaded or seeded into the device.

The systems of the invention can comprise a device to be implanted into a subject to supplement or replace the biological function of a tissue or organ.

In one embodiment, the system comprises an extra extracorporeal renal dialysis device. Although the kidney is a complex organ with an intricate vascular supply and at least 15 different cell types, the critical functions of filtration, reabsorption and excretion can be targeted with tissue engineering. The basic functional unit of the kidney, the nephron, is composed of a vascular filter, the glomerulus, and a resorptive unit, the tubule. Filtration is dependent on flow and specialized glomerular endothelial cells. The majority (50-65%) of reabsorption is performed by the proximal tubule cells using active sodium transport through the energy-dependent Na+-K+-ATPase located on the basolateral membrane. Only 5-10% of the approximately one million nephrons in each human kidney is required to sustain normal excretory function.

The design of a tissue engineered renal replacement device can then be focused on the development of a glomerular endothelial filter in conjunction with a proximal tubule device for reabsorption and excretion. The endothelial filter is specifically designed to provide physiologic flow with low thrombogenicity and maximized surface area for solute transport. The proximal tubule device, containing an appropriate number of cells for renal replacement, has optimized surface area for solute reabsorption and an outlet for urine excretion.

Several layers of molds and/or polymer scaffolds and semi-permeable membranes can be stacked to optimize filtration and reabsorption. Biologically compatible, bioresorbable and microporous polymers are used throughout for optimal cell growth and function.

Systems of the invention can also comprise a device for use in carrying out pharmacological studies of candidate drugs, to test for toxicity and efficacy of lead compounds or existing drugs, to replace suspect animal models and expensive clinical trials. Methods for conducting drug screening using tissue engineered devices are described in International Application No. PCT/US04/01098, filed Jan. 16, 2004, the contents of which are incorporated herein by reference for the description of methods to be employed.

The following examples are put forth so as to provide those of ordinary skill in the art with a complete disclosure and description of how to make and use the invention, and are not intended to limit the scope of what the inventors regard as their invention.

EXAMPLES

Example 1

Fabrication of Silicon and Poly (Dimethylsiloxane) Molds

Photolithography is the first step in micromachining silicon to define the nanoscale features that comprise the base layer. In this first step, a photosensitive surface (photoresist) was etched through the use of light. The photoresist was selectively exposed using a designed template and then the exposed areas were chemically removed in a developer. For this process, approximately 10 ml of Shipley's 1822 photoresist was used. The photoresist was spun onto the silicon wafer at 5000 rpm, resulting in a resin thickness of approximately 2 µm. The areas to be etched away were exposed in a Karl-Suss mask aligner. After exposure and development, the portions of the silicon that were to be etched into the vascular bed were visible and the parts that were not etched were protected by the photoresist.

The prepared wafer was subsequently used to perform a deep reactive ion etch using a Surface Technology Systems (STS) ion etch tool to create the channels into the silicon. An average human capillary is approximately 10-15 urn in diameter and endothelial cells are approximately 10 urn wide. Thus, fully endothelialized blood vessel of 10-15 microns in diameter necessitates a scaffold vessel diameter of 30-35 m. To mimic this structure, channels of 30-35 pm deep were etched.

The final step in the silicon fabrication process was the deposition of a release layer to ensure that the PEG-VS (polyethylene glycol-VS) gel did not adhere and tear during removal from the wafer. For this capability, a C4F8 plasma coating (similar to Teflon) layer of approximately 40 nm in thickness was deposited. This was also performed in the STS etch tool.

Poly(dimethyl siloxane) (PDMS) was used as a secondary mold; the monomer liquid was mixed with a polymerizing/cross-linking agent (Sylgard 184) at a 10:1 ratio and about 80 grams was poured onto the etched silicon wafer. The polymerization process required 2 hours at 65° C. to solidify. Increased heating time resulted in an increase in cross-link density, which yielded increased stiffness and a higher likelihood of tearing. Cured PDMS molds were excised with a square razor blade.

Example 2

Compression Molding of PLGA

Figure 15:
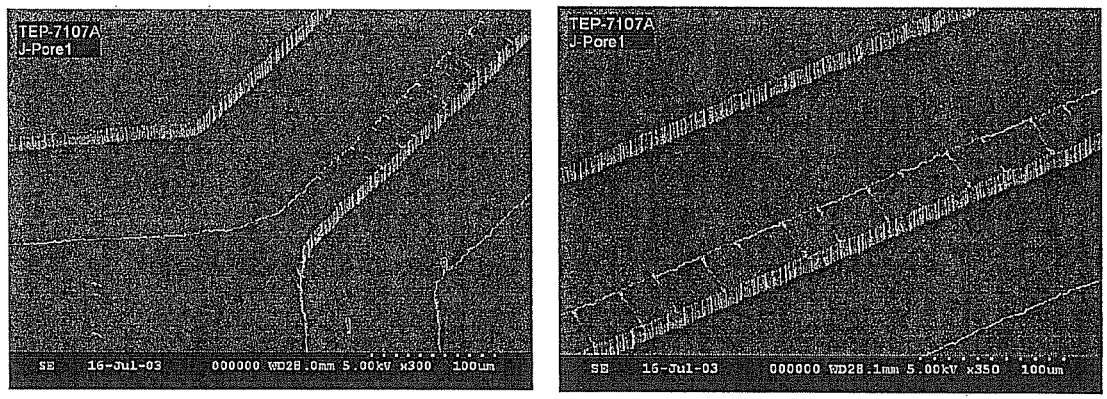
FIG. 15 depicts scanning electron microscope images of J-Pore design.
Figure 16:
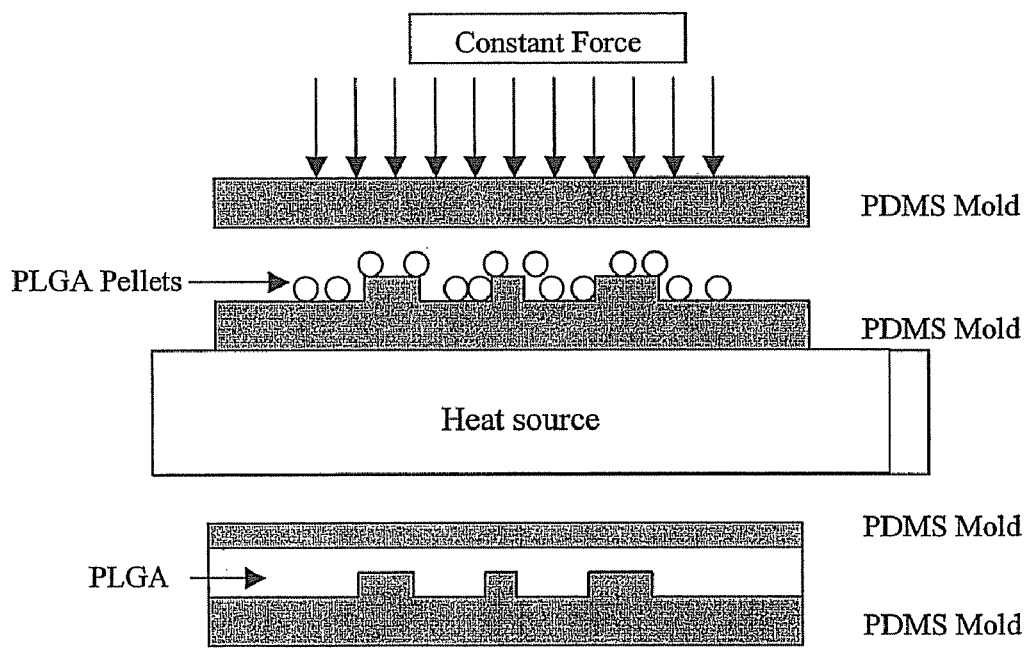
FIG. 16 depicts a schematic of the PolyLactide-co-Glycolide (PLGA) melt processing using PolyDiMethylSiloxane (PDMS) molds.
Figure 17:
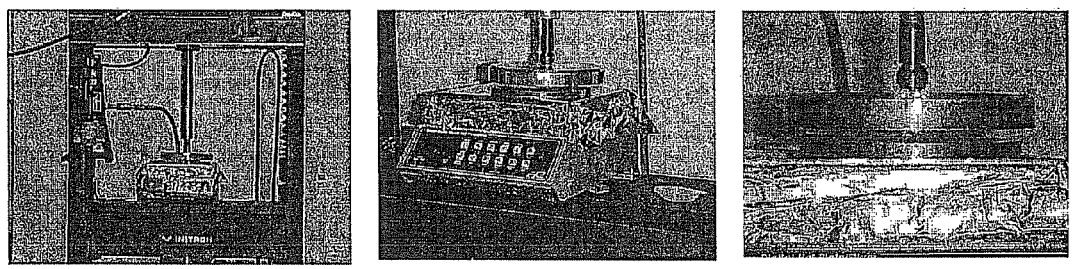
FIG. 17 depicts a melt-processing apparatus. The hotplate is for temperature control; Instron is used for application of controlled force; and the polymer pellets-PDMS-rigid plate stack are used for compression molding.

The cross-linked PDMS mold was used to press melted poly (lactide co-glycolide) (PLGA) into the desired layer structure. A PDMS mold with a test pattern called J-Pore was placed on a rigid metal plate and roughly 6 grams of Medisorb low IV PLGA 85:15 polymer pellets were spread across the entire surface of the mold (FIGS. 15,16). A top PDMS mold with an unpatterned surface was placed over the pellet-covered bottom mold, while another rigid metal plate was placed on top of the stack. The entire stack was then placed on a hotplate at a temperature exceeding the glass transition temperature (>55° C.). During heating, approximately 100-300 lbs of force was applied to the stack for 8 minutes. After 8 minutes of simultaneous heat and pressure, the stack was removed and the two rigid metal plates were removed. The PDMS stack was placed on a flat metal surface and a large metal weight was placed on top of the stack to press it during the cooling step. The stack cooled under the metal weight for approximately 5 minutes, after which the PDMS molds were peeled off from the PLGA layer and the excess PLGA was cut away.

Example 3

Connecting and Bonding the Device

The PLGA layer was placed design-side down on a piece of PDMS. A 16-gauge syringe needle was heated with a heat gun and poked through the inlets and outlets of the PLGA layer generating four through-holes in each layer. The PLGA layer was then placed on a piece of cardboard with holes punched out beneath the through-holes. About 2 inches of size 020 silastic tubing was poked through each through-hole such that about 1 centimeter protruded on the design side. The tubes were secured in place by applying a small amount of urethane around the circumference of the tube.

Urethane was allowed at least 30 minutes to dry. Any urethane and tubing on the design side of the PLGA layer was trimmed off with a sharp square razor blade.

When brought into molecular contact at a temperature above their glass transition temperature, the macroscopic interface between the surfaces of two pieces of similar polymer gradually disappeared and the interface's mechanical strength increased. This phenomenon, known as polymer welding or polymer healing, was used to bond PLGA layers. A flat piece of PLGA was placed on a piece of PDMS. A PLGA layer with the J-pore design and tubing in its inlets and outlets was placed on top of the flat layer. Applying heat with a heat gun for about 30-60 seconds bonded the layers.

Figure 18:
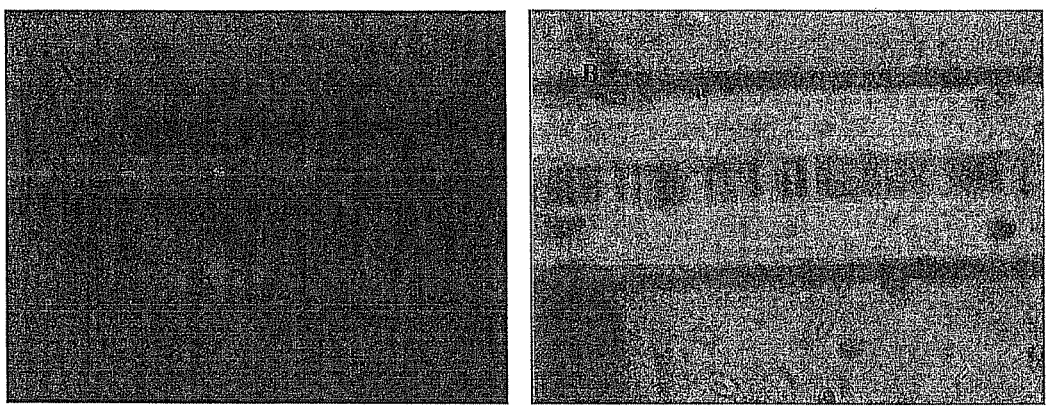
FIG. 18 depicts light microscopy images of pores between channels in a PLGA device.

Light microscopy of the pores between channels in a PLGA device (FIG. 18A) showed that pores and channels were maintained in bonding process. In FIG. 18B, pores can be seen in focus, while the channels are out of focus. These images also demonstrated that the pores became more difficult to detect after bonding, because they were clearest when the rest of the design features were out of focus.

Example 4

Testing the Microfabricated Device Using Fluorescent Beads

Figure 19:
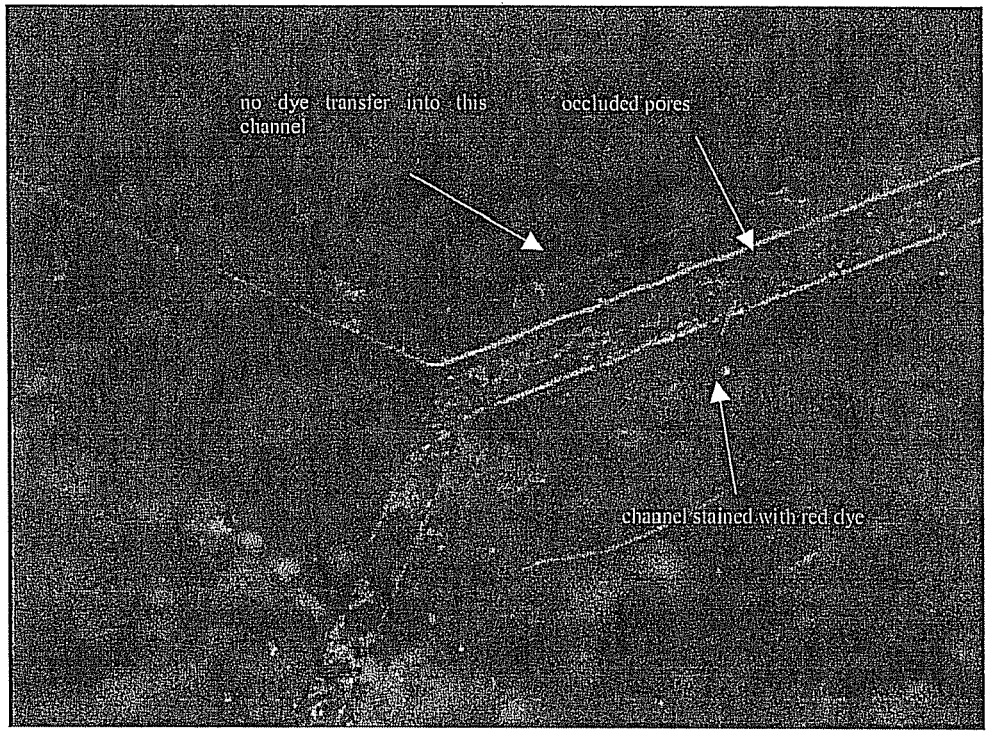
FIG. 19 depicts light microscopy images of 40-llm wide channels and pores occluded with red fluorescent beads.
Figure 20:
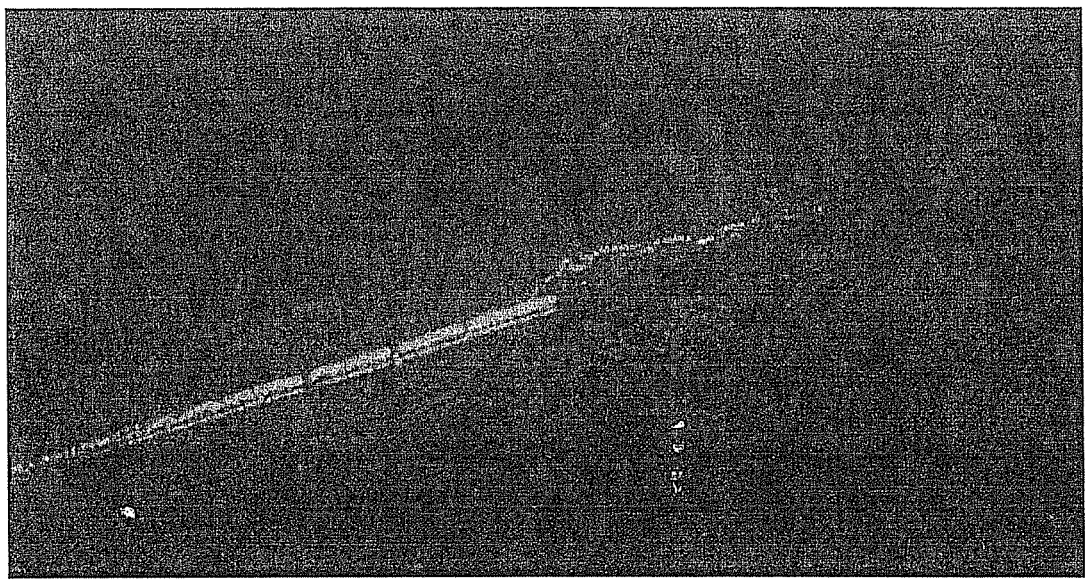
FIG. 20 depicts light microscopy images of 20-jjm-wide channels. Pores between channels were maintained in the left half of the picture and occluded in the right half. Red fluorescent beads of 1 tm in diameter were flowed through the upper channel.

For flow testing, red fluorescent beads of 1-µm in diameter were diluted in distilled water at a 1:30 concentration. A Harvard PHD2000 displacement syringe pump (Harvard Apparatus) was used with a plastic syringe to infuse the solution of red fluorescent beads into the vertical pore device at a flow rate of 10 L/min. Light microscopy showed channels of 40 µm in width and pores occluded in the bonding process (FIG. 19). Red dye was flowed through the lower channel and no red dye was detected in the upper channel. This test showed that in the absence of pores, fluid could not transfer from one channel into another. It also demonstrated that the channels were not occluded in the bonding process and fluid can flow through them. Where pores were maintained, the beads flowed through into the other channel. Many beads gathered near the pores, which made the pores fluoresce very brightly. Beads could be seen passing through the pores and then flowing within the other channel. This showed that the pores could allow fluid and small particles to pass though from one channel into another.

Figure 21:
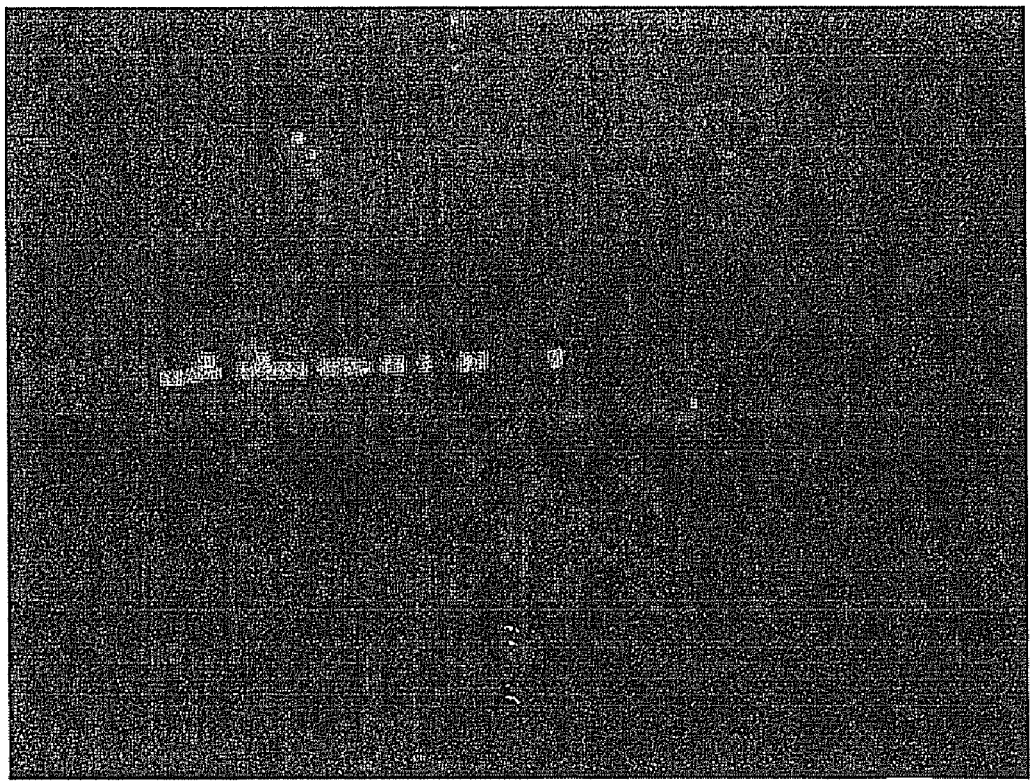
FIG. 21 depicts light microscopy images of 40-μm-wide channels. Pores between channels were maintained and 6-μm red fluorescent beads were flowed through the upper channel.

Later tests used 6-µm red fluorescent beads diluted to a 1:30 concentration. In channels that were 40-µm wide, the 6-µm red fluorescent beads were flowed through the upper channel at a flow rate of 10 µL/min. The pores between the channels were maintained. As shown in FIG. 21, the 6-µm beads could not pass through pores into other channel. They were observed lining up and forming a row along the edge of the channel, but were unable to fit through the pores. Water flowed through into the other channel, but 6-m beads were exclusively seen in the upper channel of the device.

Having thus described in detail preferred embodiments of the present invention, it is to be understood that the invention defined by the appended claims is not to be limited to particular details set forth in the above description, as many apparent variations thereof are possible without departing from the spirit or scope of the present invention. Modifications and variations of the method and apparatuses described herein will be obvious to those skilled in the art, and are intended to be encompassed by the following claims.

REFERENCES

1. G. M. Whitesides, Soft Lithography, http://www.wtec.org/loyola/nano/US.Review/0402.htm
2. Y. Xia and G. M. Whitesides, Soft Lithography, Angew. Chem. Int. Ed. 37 550 (1998.)
3. L. Leoni, D. Attiah, and T. A. Desai, Nanoporous Platforms for Cellular Sensing and Delivery, Sensors, Invited paper, Vol. 2: 111-120, 2002.
4. Tejal A. Desai, Micro- and nanoscale structures for tissue engineering constructs, *Medical Engineering & Physics*, Vol 22 (9): 595-606, 2001.
5. Tejal A. Desai, Derek J. Hansford, Lara Leoni, Matthias Essenpreis, and Mauro Ferrari'Nanoporous Anti-fouling Silicon Membranes for Itnplantable Biosensor Applications, *Biosensors and Bioelectronics,* 15 (9-10): 453-462, 2000.
6. Tejal A. Desai, Derek J. Hansford, Lawrence Kulinsky, Amir H. Nashat, Guido Rasi, Jay Tu, Yuchun. Wang, Miqin Zhang, and Mauro Ferrari. "Nanopore Technology for Biomedical Applications, *J. Biomedical Microdevices*, Vol. 2 (1), 11-40, 1999.
7. M. Ferrari, W. H. Chu, T. A. Desai, D. Hansford, G. Mazzoni and M. Zhang. Silicon Nanotechnology for Biofiltration and Immunoisolated Cell Xenografts. *Thin Films and Surfaces for Bioactivity and Biomedical Applications.* Eds. Catherine Cotell et al. Materials Research Society, vol. 414, 1996, pp. 101-106
8. U.S. Pat. No. 6,405,066, M. Essenpreis, T. A. Desai, M. Ferrari and D. J. Hansford, Implantable Analyte Sensor, Jun. 11, 2002.
9. U.S. Pat. No. 5,985,328, W. H. Chu and M. Ferrari, Micromachined Porous Membranes with Bulk Support, Nov. 16, 1999.
10. U.S. Pat. No. 6,355,270, M. Ferrari, P. J. Dehlinger, F. J. Martin, C. F. Grove and D. R. Friend, Particles for oral delivery of peptides and proteins, Mar. 12, 2002.
11. U.S. Patent Application 20030064095, F. J. Martin and A. A. Boiarski, Microfabricated Nanopore Device for Sustained Release of Therapeutic Agent, Apr. 3, 2003.
12. J. T. Borenstein, et al. W. Cheung, L. Hartman, M. R. Kaazempur-Mofrad, K. R. King, A. Sevy, M. Shin, E. J. Weinberg and J. P. Vacanti, Living Three-Dimensional Microfabricated Constructs for the Replacement Of Vital Organ Function, *Proc.* 12*th Int'l. Conf: Solid State Sensors, Actuators and Microsystems* (Transducers 2003), 1754-7 (2003).

What is claimed is:

1. A three-dimensional system comprising at least two layers, wherein each layer comprises channels divided longitudinally into two compartments by a centrally positioned membrane, and wherein each compartment includes a different cell type and the membrane has pores sized to enable only fluid communication.

2. The system of claim 1, further comprising a support element for each layer.

3. The system of claim 1, wherein the membrane further comprises a solid material contained within at least one pore of the membrane.

4. The system of claim 1, further comprising a bridge connecting two sections of the same compartment.

5. The system of claim 1, further comprising a bridge connecting a compartment of one channel to a compartment of another channel.

6. The system of claim 5, wherein the bridge connects compartments having same cell types.

7. The system of claim 5, wherein the bridge connects compartments having primary cells in one of the connected compartments and compatible cells in the other connected compartment for providing support to the primary cells.

8. A three-dimensional system comprising:
at least two layers, wherein each layer comprises channels divided longitudinally into two compartments by a centrally positioned membrane, and wherein each compartment includes a different cell type and the membrane defines pores for fluid communication between the two compartments; and
a bridge connecting a compartment of one channel to a compartment of another channel, wherein the bridge connects compartments having primary cells in one of the connected compartments and compatible cells in the other connected compartment for providing support to the primary cells.

* * * * *